(12) United States Patent
Kasianowicz et al.

(10) Patent No.: US 9,500,610 B2
(45) Date of Patent: Nov. 22, 2016

(54) SYSTEMS AND METHODS FOR CONTROLLING TEMPERATURE OF SMALL VOLUMES

(71) Applicant: National Institute of Standards and Technology, Gaithersburg, MD (US)

(72) Inventors: John J. Kasianowicz, Gaithersburg, MD (US); Joseph E. Reiner, Fredericksburg, VA (US); Arvind K. Balijepalli, Gaithersburg, MD (US); Joseph W. Robertson, Gaithersburg, MD (US); Daniel L. Burden, Wheaton, IL (US); Lisa Burden, Wheaton, IL (US)

(73) Assignee: THE UNITED STATES OF AMERICA, AS REPRESENTED BY THE SECRETARY OF COMMERCE, THE NATIONAL INSTITUTE OF STANDARDS AND TECHNOLOGY, Washington, DC (US)

(*) Notice: Subject to any disclaimer, the term of this patent is extended or adjusted under 35 U.S.C. 154(b) by 507 days.

(21) Appl. No.: 14/073,126

(22) Filed: Nov. 6, 2013

(65) Prior Publication Data

US 2014/0064324 A1  Mar. 6, 2014

Related U.S. Application Data

(60) Provisional application No. 61/722,817, filed on Nov. 6, 2012.

(51) Int. Cl.
  *G01N 25/20* (2006.01)
  *G01K 7/00* (2006.01)
  (Continued)

(52) U.S. Cl.
  CPC .................. *G01N 25/00* (2013.01); *G01K 7/16* (2013.01); *G01K 2211/00* (2013.01)

(58) Field of Classification Search
  CPC ........ G01N 25/00; G01N 25/20; G01K 1/00; G01K 7/00
  USPC ........... 374/183, 44, 45, 100, 178, 121, 120; 977/700, 742, 788, 902; 438/478
  See application file for complete search history.

(56) References Cited

U.S. PATENT DOCUMENTS

| 6,777,639 B2 | 8/2004 | Schroder et al. |
| 7,157,228 B2 | 1/2007 | Hashmi et al. |

(Continued)

FOREIGN PATENT DOCUMENTS

WO  WO2008018893  2/2008

OTHER PUBLICATIONS

Huang, X.; El-Sayed, I. H.; Qian, W.; El-Sayed, M. A. "Cancer Cell Imaging and Photothermal Therapy in the Near-Infrared Region by Using Gold Nanorods"; J. Am. Chem. Soc. 2006, 128, 2115-2120.

(Continued)

*Primary Examiner* — Gail Kaplan Verbitsky
(74) *Attorney, Agent, or Firm* — Mark E. Bandy; Rankin, Hill & Clark LLP

(57) ABSTRACT

Systems and methods for controlling the temperature of small volumes such as yoctoliter volumes, are described. The systems include one or more plasmonic nanostructures attached at or near a nanopore. Upon excitation of the plasmonic nanostructures, such as for example by exposure to laser light, the nanoparticles are rapidly heated thereby causing a change in the ionic conductance along the nanopore. The temperature change is determined from the ionic conductance. These temperature changes can be used to control rapid thermodynamic changes in molecular analytes as they interact with the nanopore.

15 Claims, 8 Drawing Sheets

(51) Int. Cl.
  G01K 1/00    (2006.01)
  G01N 25/00   (2006.01)
  G01K 7/16    (2006.01)

(56) References Cited

U.S. PATENT DOCUMENTS

| | | | |
|---|---|---|---|
| 7,248,360 B2 | 7/2007 | Horchner et al. | |
| 8,465,201 B2* | 6/2013 | Imholt | G01J 5/02 374/112 |
| 2010/0122907 A1 | 5/2010 | Stanford et al. | |
| 2010/0308848 A1* | 12/2010 | Kaul | G01N 27/127 324/693 |
| 2011/0168968 A1* | 7/2011 | Yang | B82Y 10/00 257/9 |
| 2014/0023116 A1* | 1/2014 | Ivanov | B82Y 30/00 374/183 |
| 2015/0060952 A1* | 3/2015 | Takulapalli | G01N 27/4145 257/253 |
| 2015/0119259 A1* | 4/2015 | Ju | C12Q 1/6869 506/2 |
| 2015/0146761 A1* | 5/2015 | Caraveo Frescas | H01L 29/24 374/178 |
| 2015/0325743 A1* | 11/2015 | Mi | H01L 31/03044 136/249 |
| 2015/0372040 A1* | 12/2015 | Pralle | H01L 27/14627 257/432 |
| 2016/0018269 A1* | 1/2016 | Maurer | G01K 11/20 374/121 |
| 2016/0028004 A1* | 1/2016 | Tour | H01L 45/08 257/3 |

OTHER PUBLICATIONS

Hirsch, L. R.; Stafford, R. J.; Bankson, J. A.; Sershen, S. R.; Rivera, B.; Price, R. E.; Hazle, J. D.; Halas, N. J.; West, J. L.; "Nanoshell-mediated near-infrared thermal therapy of tumors under magnetic resonance guidance"; Proc. Natl. Acad. Sci. U.S.A. 2003, 100, 13549-13554.

Day, E. S.; Morton, J. G.; West, J. L.; "Nanoparticles for Thermal Cancer Therapy"; J. Biomech. Eng. 2009, 131, 074001-1, 074001-5.

He, L.; Robertson, J. W. F.; Li, J.; Karcher, I.; Schiller, S.; Knoll, W.; Naumann, R. L. C.; "Tethered Bilayer Lipid Membranes Based on Monolayers of Thiolipids Mixed with a Complementary Dilution Molecule. 1. Incorporation of Channel Peptides"; Langmuir 2005, 21, 11666-11672.

McGillivray, D. J.; Valincius, G.; Heinrich, F.; Robertson, J. W. F.; Vanderah, D. J.; Febo-Ayala, W.; Ignatjev, I.; Losche, M.; Kasianowicz, J. J.; "Structure of Functional *Staphylococcus aureus* a-Hemolysin Channels in Tethered Bilayer Lipid Membranes"; Biophys. J. 2009, 96, 1547-1553.

Mueller, P.; Rudin, D. O.; Tien, H. T.; Wescott, W. C.; "Methods for the Formation of Single Bimolecular Lipid Membranes in Aqceous Solution"; J. Phys. Chem. 1963, 67, 534-535.

Song, L.; Hobaugh, M.; Shustak, C.; Cheley, S.; Bayley, H.; Gouaux, J.; "Structure of Staphilococcal a-Hemolysin, a Heptameric Transmembrane pore"; Science 1996, 274, 1859-1866.

Zhang, J.; Liu, Y.; Ke, Y.; Yan, H.; "Periodic Square-Like Gold Nanoparticle Arrays Templated by Self-Assembled 2D DNA Nanogrids on a Surface"; Nano Lett. 2006, 6, 248-251.

Wu, Y.; Koch, W.; Pratt, K.; "Proposed New Electrolytic Conductivity Primay Standards for KCl Solutions"; Journal of Research of the National Institute of Standards and Technology; J. Res. NIST 1991, 96, 191-201.

Cruz, R. D. C.; Martins, R. J.; Cardoso, M. J. E. De M.; Barcia, O. E.; "Volumetric Study of Aqueous Solutions of Polyethylene Glycol as a Function of the Polymer Molar Mass in the Temperature Range 283.15 to 313.15 K and 0.1 MPa"; J. Solution Chem. 2009, 38, 957-981.

Menestrina, G.; "Ionic Channels Formed by *Staphylococcus aureus* Alpha-Toxin: Voltage-Dependent Inhibition by Divalent and Trivalent Cations"; J. Membr. Biol. 1986, 90, 177-190.

Kang, X.-F.; Gu, L.-Q.; Cheley, S.; Bayley, H.; "Single Protein Pores Containing Molecular Adapters at High Temperatures"; Angew. Chem. Int. Ed. 2005, 44, 1495-1499.

Krasilnikov, O. V.; Merzlyak, P. G.; Yuldasheva, L. N.; Capistrano, M. F.; "Protein electrostriction: a possibility of elastic deformation of the a-hemolysin channel by the applied field"; Eur. Biophys. J. 2005, 34, 997-1006.

Robertson, J. W. F.; Kasianowicz, J. J.; Reiner, J. E.; "Changes in ion channel geometry resolved to sub-° angstr̈om precision via single molecule mass spectrometry"; J. Phys.-Condens. Mat. 2010, 22, 454108.

Lathrop, D. K.; Ervin, E. N.; Barrall, G. A.; Keehan, M. G.; Kawano, R.; Krupka, M. A.; White, H. S.; Hibbs, A. H.; "Monitoring the Escape of DNA from a Nanopore Using an Alternating Current Signal"; J. Am. Chem. Soc. 2010, 132, 1878-1885.

Robertson, J. W. F.; Rodrigues, C. G.; Stanford, V. M.; Rubinson, K. A.; Krasilnikov, O. V.; Kasianowicz, J. J.; "Single-molecule mass spectometry in solution using a solitary nanopore"; Proc. Natl. Acad. Sci. U.S.A. 2007, 104, 8207-8211.

Reiner, J. E.; Kasianowicz, J. J.; Nablo, B. J.; Robertson, J. W. F.; "Theory for polymer analysis using nanopore-based single-molecule mass spectrometry"; Proc. Natl. Acad. Sci. U.S.A. 2010, 107, 12080-12085.

Bezrukov, S. M.; Vodyanoy, I.; Brutyan, R.; Kasianowicz, J. J.; "Dynamics and Free Energy of Polymers Partitioning into a Nanoscale Pore"; Macromolecules 1996, 29, 8517-8522.

Bezrukov, S. M.; Krasilnikov, O. V.; Yuldasheva, L. N.; Berezhkovskii, A. M.; Rodrigues, C. G.; "Field-Dependent Effect of Crown Ether (18-Crown-6) on Ionic Conductance of a-Hemolysin Channels"; Biophys. J. 2004, 87, 3162-3171.

Rodrigues, C. G.; Machado, D. C.; Chevtchenko, S. F.; Krasilnikov, O. V.; "Mechanism of KCl Enhancement in Detection of Nonionic Polymers by Nanopore Sensors"; Biophys. J. 2008, 95, 5186-5192.

Henrickson, S.; Misakian, M.; Robertson, B.; Kasianowicz, J. J.; "Driven DNA Transport into an Asymmetric Nanometer-Scale Pore"; Phys. Rev. Lett. 2000, 85, 3057-3060.

Ambjornsson, T.; Apell, S. P.; Konkoli, Z.; Di Marzio, E. A.; Kasianowicz, J. J.; "Charged polymer membrane translocation"; J. Chem. Phys. 2002, 117, 4063-4073.

Muthukumar, M. ; "Theory of capture rate in polymer translocation"; J. Chem. Phys. 2010, 132, 195101.

Chan, J.; Popov, J.; Kolisnek-Kehl, S.; Leaist, D.; "Soret Coefficients for Aqueous Polyethylene Glycol Solutions and Some Tests of the Segmental Model of Polymer Thermal Diffusion"; J. Solution Chem. 2003, 32, 197-214.

Henriquez, R.; Ito, T.; Sun, L.; Crooks, R. M.; "The resurgence of Coulter counting for analyzing nanoscale objects"; Analyst 2004, 129, 478-482.

Kasianowicz, J. J.; Robertson, J. W. F.; Chan, E. R.; Reiner, J. E.; Stanford, V. M.; "Nanoscopic Porous Sensors"; Annu. Rev. Anal. Chem. 2008, 1, 737-766.

Reiner, J. E.; Balijepalli, A.; Robertson, J. W. F.; Campbell, J.; Suehle, J.; Kasianowicz, J. J.; "Disease Detection and Management via Single Nanopore-Based Sensors"; Chem. Rev. 2012, 112, 6431-6451.

Bezrukov, S.; Kasianowicz, J. J.; "Current noise reveals protonation kinetics and number of ionizable sites in an open protein ion channel"; Phys. Rev. Lett. 1993, 70, 2352-2355.

Kasianowicz, J. J.; Bezrukov, S. M.; "Protonation Dynamics of the a-Toxin Ion Channel from Spectral Analysis of pH-Dependent Current Fluctuations"; Biophys. J. 1995, 69, 94-105.

Kasianowicz, J. J.; Brandin, E.; Branton, D.; Deamer, D. W.; "Characterization of individual polynucleotide molecules using a membrane channel"; Proc. Natl. Acad. Sci. U.S.A. 1996, 93, 13770-13773.

Mathe, J.; Aksimentiev, A.; Nelson, D. R.; Schulten, K.; Meller, A.; "Orientation discrimination of single-stranded DNA inside the A-hemolysin membrane channel"; Proc. Natl. Acad. Sci. U.S.A. No. 2005, 102, 12377-12382.

Li, J.; Stein, D.; McMullan, C.; Branton, D.; Aziz, M.; Golovchenko, J. A.; "Ion-beam sculpting at nanometre lenght scales"; Nature 2001, 412, 166-169.

(56) References Cited

OTHER PUBLICATIONS

Halverson, K. M.; Panchal, R. G.; Nguyen, T. L.; Gussio, R.; Little, S. F.; Misakian, M.; Bavari, S.; Kasianowicz, J. J.; "Anthrax Biosensor, Protective Antigen Ion Channel Asymmetric Blockade"; J. Biol. Chem. 2005, 280, 34056-34062.

Merchant, C. A.; Healy, K.; Wanunu, M.; Ray, V.; Peterman, N.; Bartel, J.; Fischbein, M. D.; Yenta, K.; Luo, Z.; Johnson, A. T. C.; Drndic, M.; "DNA Translocation through Graphene Nanopores"; Nano Lett. 2010, 10, 2915-2921.

Schneider, G. F.; Kowalczyk, S. W.; Calado, V. E.; Pandraud, G.; Zandbergen, H. W.; Vandersypen, L. M. K.; Dekker, C.; "DNA Translocation through Graphene Nanopores"; Nano Lett. 2010, 10, 3163-3167.

Garaj, S.; Hubbard, W.; Reina, A.; Kong, J.; Branton, D.; Golovchenko, J. A.; "Graphene as a subnanometre trans-electrode membrane"; Nature 2010, 467, 190-U73.

Kasianowicz, J. J.; Henrickson, S.; Weetall, H.; Robertson, B.; "Simultaneous Multianalyte Detection with a Nanometer-Scale Pore"; Anal. Chem. 2001, 73, 2268-2272.

Oukhaled, G.; Mathe, J.; Biance, A.-L.; Bacri, L.; Betton, J.-M.; Lairez, D.; Pelta, J.; Auvray, L.; "Unfolding of Proteins and Long Transient Conformations Detected by Single Nanopore Recording"; Phys. Rev. Lett. 2007, 98, 158101.

Fologea, D.; Ledden, B.; McNabb, D. S.; Li, J.; "Electrical characterization of protein molecules by a solid-state nanopore"; Appl. Phys. Lett. 2007, 91, 053901.

Payet, L.; Martinho, M.; Pastoriza-Gallego, M.; Betton, J.M.; Auvray, L.; Pelta, J.; Mathe, J.; "Thermal Unfolding of Proteins Probed at the Single Molecule Level Using Nanopores"; Anal. Chem. 2012, 84, 4071-4076.

Stefureac, R.; Long, Y.T.; Kraatz, H.B.; Howard, P.; Lee, J. S.; "Transport of R-Helical Peptides through R-Hemolysin and Aerolysin Pores"; Biochemistry 2006, 45, 9172-9179.

Kullman, L.; Winterhalter, M.; Bezrukov, S. M.; "Transport of Maltodextrins through Maltoporin: A Single-Channel Study"; Biophys. J. 2002, 82, 803-812.

Wendell, D.; Jing, P.; Geng, J.; Subramaniam, V.; Lee, T. J.; Montemagno, C.; Guo, P.; "Translocation of double-stranded DNA through membrane-adapted phi29 motor protein nanopores"; Nat. Nanotech. 2009, 4, 765-772.

Storm, A. J.; Chen, J. H.; Ling, X. S.; Zandbergen, H. W.; Dekker, C.; "Fabrication of solid-state nanopores with single-nanometre precision"; Nat. Mater. 2003, 2, 537-540.

Kim, M. J.; Wanunu, M.; Bell, D. C.; Meller, A.; "Rapid Fabrication of Uniformly Sized Nanopores and Nanopore Arrays for Parallel DNA Analysis"; Adv. Mater. 2006, 18, 3149-3153.

Neher, E.; Sakmann, B.; "Single-channel Currents recorded from membrane of denervated frog muscle fibers"; Nature; 1976, 260, 799-802.

Ainavarapu, R. K.; Brujic, J.; Huang, H. H.; Wiita, A. P.; Lu, H.; Li, L.; Walther, K. A.; Carrion-Vazquez, M.; Li, H.; Fernandez, J. M.; "Contour Length and Refolding Rate of a Small Protein Controlled by Engineered Disulfide Bonds"; Biophys. J. 2007, 92, 225-233.

Ha, H.; Zhuang, X.; Kim, H.; Orr, J.; Williamson, J.; Chu, S.; "Ligand-induced conformational changes observed in single RNA molecules"; Proc. Natl. Acad. Sci.; U.S.A. 1999, 96, 9077-9082.

Ha, T.; Ting, A.; Liang, J.; Caldwell, W.; Deniz, A.; Chemla, D.; Schultz, P.; Weiss, S.; "Single-molecule fluorescence spectroscopy of enzyme conformational dynamics and cleavage mechanism"; Proc. Natl. Acad. Sci.; U.S.A. 1999, 96, 893-898.

Weiss, S.; "Measuring conformational dynamics of biomolecules by single molecule fluorescence spectroscopy"; Nat. Struct. Biol.; 2000, 7, 724-729.

Schenter, G.; Lu, H.; Xie, X.; "Statistical Analyses and Theoretical Models of Single-Molecule Enzymatic Dynamics"; J. Phys. Chem. A 1999, 103, 10477-10488.

Hartridge, H.; Roughton, F.; "A Method of Measuring the Velocity of Very Rapid Chemical Reactions"; Proc. Royal Soc. Lond. A 1923, 104, 376-394.

Chance, B. J.; "The accelerated flow method for rapid reactions"; Frankl. Inst. 1940, 229, 613-640.

Bayley, P.; Anson, M.; "Stopped-Flow Circular Dichroism: A New Fast-Kinetic System"; Biopolymers 1974, 13, 401-405.

Lillo, M. P.; Szpikowska, B. K.; Mas, M. T.; Sutin, J. D.; Beechem, J. M.; "Real-Time Measurement of Multiple Intramolecular Distances during Protein Folding Reactions: A Multisite Stopped-Flow Fluorescence Energy-Transfer Study of Yeast Phosphoglycerate Kinase"; Biochemistry 1997, 36, 11273-11281.

Green, D.; Lane, J.; Wing, R.; "A Standard Session Stopped-Flow NMR Tube"; Appl. Spectrosc. 1987, 41, 847-851.

Thorneley, R. N.; Ashby, G.; Howarth, J. V.; Millar, N. C.; Gutfreund, H.; "A transient-kinetic study of the nitrogenase of Klebsiella pneumoniae by stopped-flow calorimetry"; Biochem. J. 1989, 264, 657-661.

Barman, T. E.; Bellamy, S. R. W.; Gutfreund, H.; Halford, S. E.; Lionne, C.; "The identification of chemical intermediates in enzyme catalysis by the rapid quench-flow technique"; Cell. Mol. Life Sci. 2006, 63, 2571-2583.

Kuwajima, K.; Yamaya, H.; Miwa, S.; Sugai, S.; Nagamura, T.; "Rapid formation of secondary structure framework in protein folding studied by stopped-flow circular dichroism"; Febs Lett. 1987, 221, 115-118.

Antonini, G.; Malatesta, F.; Sarti, P.; Brunori, M.; "Proton pumping by cytochrome oxidase as studied by time-resolved stopped-flow spectrophotometry"| Proc. Natl. Acad. Sci. U.S.A. 1993, 90, 5949-5953.

Christianson, M. D.; Tan, E. H. P.; Landis, C. R.; "Stopped-Flow NMR: Determining the Kinetics of [rac-(C2H4(1-indenyl)2)ZrMe][MeB(C6F5)3]-Catalyzed Polymerization of 1-Hexene by Direct Observation"; J. Am. Chem. Soc. 2010, 132, 11461-11463.

Gaikwad, A.; Gomezhens, A.; Perezbendito, D.; "Use of stopped-flow fluorescence polarization immunoassay in drug determinations"; Anal. Chim. Acta 1993, 280, 129-135.

Harvey, R. A.; Borcherd, W. O.; "Variable-Ratio Stopped-Flow Mixing Device"; Anal. Chem. 1972, 44, 1926-1928.

Suh, K.; Kim, Y.; Lee, H.; "Capillary Force Lithography"; Wiley-VCH Verlag GmbH, D-69469 Weinheim, 2001; Adv. Mater. 2001, 13, 1386-1389.

Regenfuss, P.; Clegg, R. M.; Fulwyler, M. J.; Barrantes, F. J.; Jovin, T. M.; "Mixing liquids in microseconds"; Rev. Sci. Instrum. 1985, 56, 283.

Pines, E.; Huppert, D.; "Kinetics of Proton Transfer in Ice Via the PH-Jump Method: Evaluation of the Proton Diffusion Rate in Polycrystalline Doped Ice"; Chem. Phys. Lett. 1985, 116, 295-301.

Benz, R.; Lauger, P.; Janko, K.; "Transport Kinetics of Hydrophobic Ions Membranes Charge-Pulse Relaxation Studies"; Biochim. Biophys. Acta 1976, 455, 701-720.

Stark, G.; Ketterer, B.; Benz, R.; Lauger, P.; "The Rate Constants of Valinomycin-Mediated Ion Transport Through Thin Lipid Membranes"; Biophys. J. 1971, 11, 981-994.

Kellermayer, M. S.; Smith, S. B.; Granzier, H. L.; Bustamante, C.; "Folding-Unfolding Transitions in Single Titin Molecules Characterized with Laser Tweezers"; Science 1997, 276, 1112-1116.

Schlierf, M.; Li, H.; Fernandez, J. M.; "The unfolding kinetics of ubiquitin captured with single-molecule force-clamp techniques"; Proc. Natl. Acad. Sci. U.S.A. 2004, 101, 7299-7304.

Dudko, O. K.; Mathe, J.; Meller, A.; "Nanopore Force Spectroscopy Tools for Analyzing Single Biomolecular Complexes"; Meth. Enzymol. 2010, 474, 565-589.

Czerlinski, G.; Eigen, M. Z.; "Eine Temperatursprungmethode zur Untersuchung chemischer Relaxation"; Elektrochem. 1959, 63, 652-661.

Eigen, M.; "Immeasurably fast reactions"; Nobel Lecture 1967, 11, 1963-1979.

Hoffmann, H.; Yeager, E.; Steuhr, J.; "Laser Temperature Jump Apparatus for Relaxation Studies in Electrolytic Solutions"; Rev. Sci. Instrum. 1968, 39, 649-653.

Beitz, J.; Flynn, G.; Turner, D.; Sutin, N. J.; "The Stimulated Raman Effect. A new Source of Laser Temperature-Jump Heating"; Am. Chem. Soc. 1970, 92, p. 4130-4132.

(56) References Cited

OTHER PUBLICATIONS

Turner, D.; Sutin, N.; Beitz, J.; Flynn, G.; "Laser Raman Temperature-Jump Study of the Kinetics of the Triiodide Equilibrium. Relaxation Times in the 10-8-10-7 Second Range"; J. Am. Chem. Soc. 1972, 94, 1554-1559.
Smith, J.; McCray, J.; Hibberd, M.; Goldman, Y.; "Holmium laser temperature jump apparatus for kinetic studies of muscle contraction"; Rev. Sc. Instrum. 1989, 60, 231-236.
Chen, S.; Lee, I.; Tolbert, W.; Wen, X.; Dlott, D.; "Applications of Ultrafast Temperature Jump Spectroscopy to Condensed Phase Molecular Dynamics"; J. Phys. Chem. 1992, 96, 7178-7186.
Phillips, C.; Mizutani, Y.; Hochstrasser, R.; "Ultrafast thermally induced unfolding of RNase A"; Proc. Natl. Acad. Sci. U.S.A. 1995, 92, 7292-7296.
Ballew, R. M.; Sabelko, J.; Gruebele, M.; "Direct observation of fast protein folding: The initial collapse of apomyoglobin"; Proc. Natl. Acad. Sci. U.S.A. 1996, 93, 5759-5764.
Sikes, H. D.; Smalley, J.; Dudek, S.; Cook, A.; Newton, M.; Chidsey, C.; Feldberg, S. W.; "Rapid Electron Tunneling Through Oligophenylenevinylene Bridges"; Science 2001, 291, 1519-1523.
Holmstrom, E. D.; Nesbitt, D. J.; "Real-Time Infrared Overtone Laser Control of Temperature in Picoliter H2O Samples: "Nanobathtubs" for Single Molecule Microscopy"; J. Phys. Chem. Lett. 2010, 1, 2264-2268.
Knoll, W.; "Interfaces and Thin Films as Seen by Bound Electromagnetic Waves"; Annu. Rev. Phys. Chem. 1998, 49, 569-638.
Coronado, E. A.; Encina, E. R.; Stefani, F. D.; "Optical properties of metallic nanoparticles: manipulating light, heat and forces at the nanoscale"; Nanoscale 2011, 3, 4042.
Halas, N. J.; Lal, S.; Chang, W.-S.; Link, S.; Nordlander, P.; "Plasmons in Strongly Coupled Metallic Nanostructures"; Chem. Rev. 2011, 111, 3913-3961.
Seol, Y.; Carpenter, A. E.; Perkins, T. T.; "Gold nanoparticles: enhanced optical trapping and sensitivity coupled with significant heating". Opt. Lett. 2006, 31, 2429-2431.
Jain, P. K.; Huang, X.; El-Sayed, I. H.; El-Sayed, M. A.; "Noble Metals on the Nanoscale: Optical and Photothermal Properties and Some Applications in Imaging, Sensing, Biology, and Medicine"; Acc. Chem. Res. 2008, 41, 1578-1586.
Urban, A. S.; Fedoruk, M.; Horton, M. R.; Rädler, J. O.; Stefani, F. D.; Feldmann, J.; "Controlled Nanometric Phase Transitions of Phospholipid Membranes by Plasmonic Heating of Single Gold Nanoparticles"; Nano Lett. 2009, 9, 2903-2908.
Bendix, P. M.; Reihani, S. N. S.; Oddershede, L. B.; "Direct Measurements of Heating by Electromagnetically Trapped Gold Nanoparticles on Supported Lipid Bilayers"; ACS Nano 2010, 4, 2256-2262.
Jo, W.; Lee, J. H.; Kim, M. J.; "Temperature measurement in a single patterned gold nanorod cluster using laser-induced fluorescence"; J. Nanopart. Res. 2012, 14, 699.
Carlson, M. T.; Khan, A.; Richardson, H. H.; "Local Temperature Determination of Optically Excited Nanoparticles and Nanodots"; Nano Lett. 2011, 11, 1061-1069.
Kumar, S.; Tao, C.; Chien, M.; Hellner, B.; Balijepalli, A.; Robertson, J. W. F.; Li, Z.; Russo, J. J.; Reiner, J. E.; Kasianowicz, J.J.; Ju, J.; "PEG-Labeled Nucleotides and Nanopore Detection for Single Molecule DNA Sequencing by Synthesis"; Sci Rep 2012, 2, 684.
Cavicchi, R.; Suehle, J.; Kreider, K.; Gaitan, M.; Chaparala, P.; "Fast Temperature Program Sensing for Micro-Hotplate Gas Sensors"; IEEE Electron Dev. Lett. 1995, 16, 286-288.
Kunt, T.; McAvoy, T.; Cavicchi, R.; Semancik, S.; "Optimization of temperature programmed sensing for gas identification using micro-hotplate sensors"; Sensor Actuat. B 1998, 53, 24-43.
Meier, D. C.; Raman, B.; Semancik, S; "Detecting Chemical Hazards with Temperature-Programmed Microsensors: Overcoming Complex Analytical Problems with Multidimensional Databases"; Annu. Rev. Anal. Chem. 2009, 2, 463-484.
Jing Yao; Beiying Liu; Feng Qin; "Rapid Temperature Jump by Infrared Diode Laser Irradiation for Patch-Clamp Studies"; Biophysical Journal vol. 96; May 2009 3611-3619.
John F. Smalley; Stephen W. Feldberg; Christopher E. D. Chidsey; Matthew R. Linford; Marshall D. Newton; Yi-Ping Lid; "The Kinetics of Electron Transfer through Ferrocene-Terminated Alkanethiol Monolayers on Gold"; J. Phys. Chem. 1995, 99, 13141-13149.
Payet, L.; Martinho, M; Pastoriza-Gallego, M.; Betton, J.; Auvray, L.; Pelta, J.; Mathe, J.; "Thermal Unfolding of Proteins Probed at the Single Molecule Level Using Nanopores"; 2012 American Chem. Society; Anal. Chem., 84, 4071-4076.
Jonsson, M; Dekker, C.; "Plasmonic Nanopore for Eelctrical Profiling of Optical Intensity Landscapes"; 2013 American Chem. Society; Nano Lett. 2013, 1029-1033.
Belkin, M.; Maffeo, C.; Wells, D.; Aksimentiev, A.; "Stretching and Controlled Motion of Single-Stranded DNA in Locally Heated Solid-State Nanopores"; ACS Nano; 2013 American Chem. Society; vol. 7, 6816-6824.
Balzarotti, F.; Stefani, F.; "Plasmonics Meets Far-Field Optical Nanoscopy"; ACS Nano; 2012 American Chem. Society; vol. 6, 4580-4584.
Reiner, J. E.; Kasianowicz, J. J.; Nablo, B. J.; Robertson, J. W. F.; "Theory for polymer analysis using nanopore-based single-molecule mass spectometry"; Proc. Natl. Acad. Sci. U.S.A. No. 2010, 107, 12080-12085.
McGillivray, D. J.; Valincius, G.; Vanderah, D. J.; Febo-Ayala, W., Woodward, J. T.; Heinrich, F.; Kasianowicz, J. J.; Lösche, M.; "Molecular-scale structural and functional characterization of sparsely tethered bilayer lipid membranes"; Biointerphases 2007, 2,21-33.
Vockenroth I.K., Ohm, C., Robertson, J. W. F., McGillivray, D. J., Lösche, M., Köper, I.; "Stable insulating tethered bilayer lipid membranes"; Biointerphases 2008, vol. 3, FA68-FA73.
Smalley, J.; Sachs, S.; Chidsey, C.; Dudek, S.; Sikes, H. D.; Creager, S.; Yu, C.; Feldberg, S. W.; Newton, M.; "Interfacial Electron-Transfer Kinetics of Ferrocene through Oligophenyleneethynylene Bridges Attached to Gold Electrodes as Constituents of Self-Assembled Monolayers: Observation of a Nonmonotonic Distance Dependence"; J. Am. Chem. Soc. 2004, 126, 14620-14630.
Svoboda, K., Block, S. M.; "Optical trapping of metallic Rayleigh particles"; Opt. Lett. 1994, vol. 19, 930-932.
Sassaroli, E.; Li, K. C. P.; O'Neill, B. E.; "Numerical investigation of heating of a gold nanoparticle and the surrounding microenvironment by nanosecond laser pulses for nanomedicine applications"; Phys. Med. Biol. 2009, 54, 5541-5560.
Marshall, M. M.; Yang, J.; Hall, A. R.; "Direct and Transmission Milling of Suspended Silicon Nitride Membranes With a Focused Helium Ion Beam"; Scanning 2012, 34, 101-106.
Johnson, P., Christy, R.; "Optical Constants of the Noble Metal"; Phys Rev B 1972, vol. 6, 4370-4379.
McGillivray, D. J.; Valincius, G.; Heinrich, F.; Robertson, J. W. F.; Vanderah, D. J.; Febo-Ayala, W.; Ignatjev, I.; Lösche, M.; Kasianowicz, J. J.; "Structure of Functional *Staphylococcus aureus* a-Hemolysin Channels in Tethered Bilayer Lipid Membranes"; Biophys. J. 2009, 96, 1547-1553.

* cited by examiner

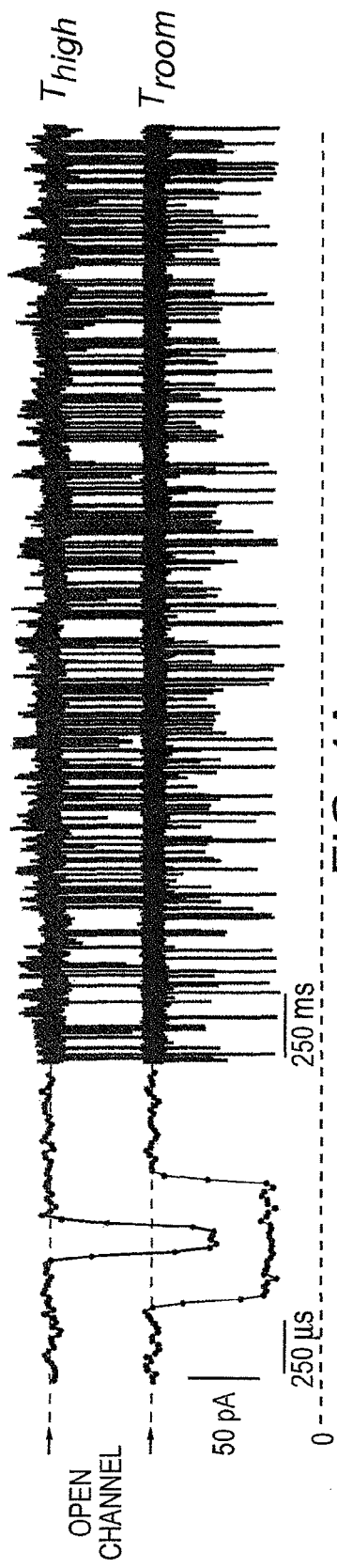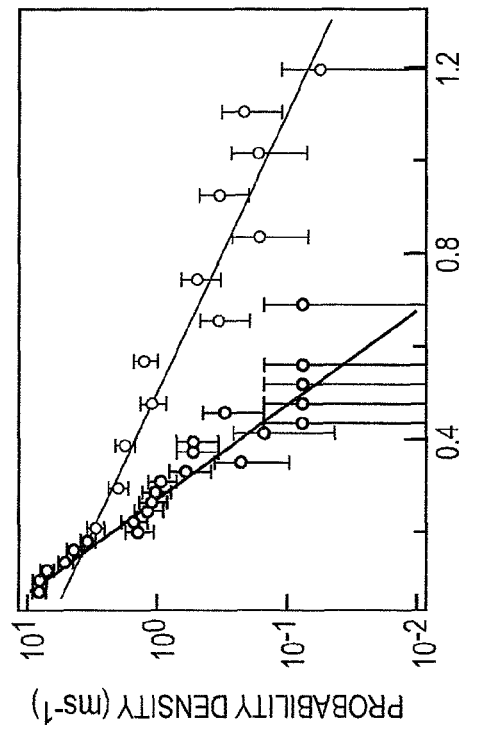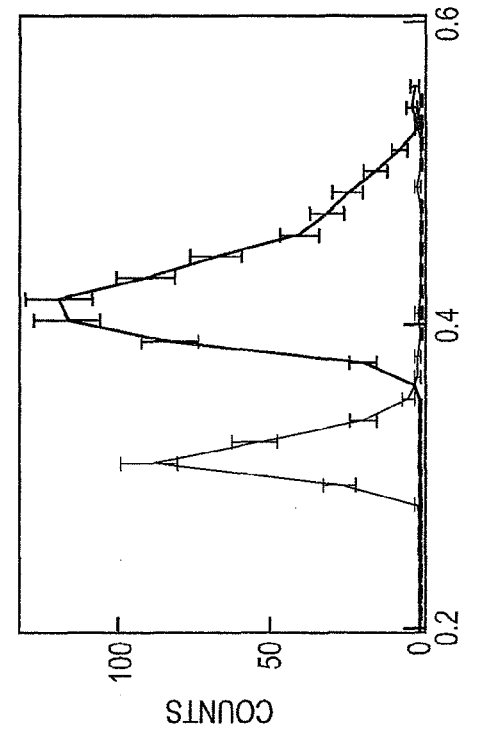
FIG. 4A
FIG. 4B
FIG. 4C

SYSTEMS AND METHODS FOR CONTROLLING TEMPERATURE OF SMALL VOLUMES

CROSS REFERENCES TO RELATED APPLICATIONS

This application claims priority from U.S. provisional application Ser. No. 61/722,817 filed on Nov. 6, 2012.

FIELD

The present subject matter relates to systems and methods for controlling and/or measuring temperature of small volumes such as for example, yoctoliter volumes. The present subject matter also relates to methods for analyzing polymers or other molecules.

BACKGROUND

The equilibrium state of a chemical or biological system is determined by many physical and chemical variables. Changes in one or more of these variables drive the system into a new steady state. Measurement of relaxation times provides information about the underlying properties of the system. The behavior of molecules along reaction pathways and the inter- and intra-molecular dynamics are best obtained using single molecule measurement techniques. A less explored regime involves isolation of the thermodynamic perturbation (e.g., temperature, pressure, chemical binding) on a single molecule and the subsequent observation of that same molecule. This strategy represents the ultimate sensitivity in reaction measurements because it isolates the internal degrees of freedom of a single molecule.

Over the last century, a variety of techniques have been developed to measure reaction rates in chemistry and biology. The most influential of these techniques relies on rapid mixing of reactant solutions (e.g., continuous flow/quenched flow, and stop-flow methods). In the stopped flow method, solutions containing different molecular species are driven into a mixing chamber within milliseconds, and the flow of reactants is abruptly stopped. The progress of the reaction is then monitored by following either an optical property (e.g., absorption, circular dichroism, fluorescence emission), the NMR signature of a reactant, or calorimetry. The stopped flow method has proved to be a seminal tool to probe the kinetics of enzyme activity, protein folding, proton pumping, polymerization, and drug interactions. The stopped flow method was initially limited to reactions with relatively slow time constants (t>1 s). However, variations on techniques to deliver the reactants in different ratios and the ability to mix liquids together more rapidly promise to enhance the utility of stopped flow methods and increase their bandwidths.

Other techniques were developed to study more rapid chemical and polymer kinetics. These include microfluidic and nanofluidic mixing, and relaxation methods that rapidly perturb a system from equilibrium by changes in pressure, or local chemical species concentration induced by pulses of laser light, ionic current, electrostatic potential, or mechanical force. The latter three methods allow for kinetic analysis at the nanometer length scale.

In the late 1950s, an ability to rapidly perturb solution temperature (T-jump) provided yet another means to measure what were considered at the time to be "immeasurably fast" diffusion-controlled reactions. Initial T-jump studies discharged capacitors to rapidly heat relatively large volumes of solution in microseconds. This technology was brought to the nanosecond domain with Q-switched lasers, and the temperature was estimated via a change in the optical absorbance of a tracer molecule. Infrared absorbing dyes were used to convert laser energy into heat over picosecond timescales, which enabled the study of rapid protein unfolding (e.g., RNaseA) and folding (e.g., apomyoglobin) or interfacial electron transfer reactions. Recently, an infrared laser (1445 nm) was used to directly excite an OH-stretch mode in water, leading to an increase in the temperature of picoliter volumes.

Most laser-based techniques require post processing (i.e., pump-probe, fluorescence lifetime) to deduce the local temperature changes, which limits the ability to accurately measure solution temperature in real time. In addition, each pulse from a Q-switched ultrafast laser represents an entire experiment, where the solution temperature initially increases to a predefined value and then relaxes to room temperature. A major improvement in the technique would expand the laser induced T-jump method to longer timescales in which a complex temporal profile of the temperature could be precisely controlled. This requires a much more localized heat source and an ability to measure the temperature of exceptionally small fluid volumes.

SUMMARY

The difficulties and drawbacks associated with previously known practices are addressed in the present systems and methods as follows.

In one aspect, the present subject matter provides a system for measuring temperature at a nanopore. The system comprises a substrate defining a surface and at least one nanopore. The system also comprises a plasmonic structure disposed proximate the nanopore. The system also comprises an ionic conducting solution which bathes the nanopore and the plasmonic structure. The system also comprises a light source capable of emitting light of sufficient intensity and wavelength to excite the plasmonic structure. And, the system also comprises an ionic current measuring assembly configured to measure changes in ionic conductance proximate to the nanopore upon excitation of the plasmonic structure resulting from emission of light from the light source. Changes in ionic conductance measured by the ionic current measuring assembly are used to determine temperature or temperature changes at the nanopore.

In yet another aspect, the present subject matter provides a method for measuring temperature at a nanopore. The method comprises providing a plasmonic structure. The method also comprises affixing the plasmonic structure proximate the nanopore. The method also comprises emitting light of sufficient intensity and wavelength to excite the plasmonic structure and induce a change in temperature. The method also comprises measuring changes in ionic conductance proximate the nanopore. The changes in ionic conductance are used to determine temperature or temperature changes at the nanopore.

In yet another aspect, the present subject matter provides a method for analyzing polymers. The method comprises providing plasmonic nanostructures. The method also comprises providing a surface containing a nanopore. The method additionally comprises affixing the plasmonic nanostructures proximate the nanopore. The method additionally comprises disposing a polymer to be analyzed in the nanopore. The method additionally comprises emitting light of sufficient intensity and wavelength to excite the plasmonic nanostructures and induce a change in temperature within the nanopore. And, the method also comprises analyzing the polymer disposed in the nanopore by assessing of the change in temperature within the nanopore.

And, in yet another aspect, the present subject matter provides a method for calculating the temperature of polymers. The method comprises providing plasmonic nanostructures. The method also comprises providing a surface containing a nanopore. The method additionally comprises affixing the plasmonic nanostructures proximate the nanopore. The method also comprises disposing a polymer to be analyzed in the nanopore. The method also comprises emitting light of sufficient intensity and wavelength to excite the plasmonic nanostructures and induce a change in temperature within the nanopore. And the method also comprises determining the temperature of the polymer disposed in the nanopore by use of the change in temperature within the nanopore.

As will be realized, the subject matter described herein is capable of other and different embodiments and its several details are capable of modifications in various respects, all without departing from the claimed subject matter. Accordingly, the drawings and description are to be regarded as illustrative and not restrictive.

BRIEF DESCRIPTION OF THE DRAWINGS

FIG. 4A is a graph of ionic current for a single nanopore over time at two different temperatures.

FIG. 4B is a histogram of relative current blockages that shift to a lesser occluded state at elevated temperature.

FIG. 4C is a histogram of PEG residence times in a nanopore shifting to shorter-lived status.

DETAILED DESCRIPTION OF THE EMBODIMENTS

The ability to perturb large ensembles of molecules from equilibrium led to major advances in understanding reaction mechanisms in chemistry and biology. The present subject matter enables precise control, measurement, and use of rapid temperature changes of fluid volumes that are commensurate with the size of single molecules. The methods of the present subject matter are based at least in part, on the coupling of plasmonic structures such as for example, metallic nanoparticles or other nanostructures adjacent to a single nanometer-scale protein ion channel or nanopore as referred to herein. Visible laser light incident on the nanoparticles causes a rapid and large increase of the solution temperature, which is measured by the change in the nanopore ionic conductance. The temperature shift affects the ability of individual molecules to enter into and interact with the nanopore. The present subject matter can significantly improve sensor systems and force measurements based on single nanopores, thereby enabling a method for single molecule thermodynamics and single molecule kinetics.

The highly confined surface plasmon resonance effect in gold nanoparticles enhances the absorption of light by the particle, thereby increasing its temperature, essentially instantaneously, i.e., ps to ns timescales, as compared to heating water with an infrared laser (µs to ms timescales). This property has been used in many bio-related applications including imaging and cancer therapies. By attaching gold nanoparticles to individual nanometer-scale pores, and optically exciting the nanoparticles, the time dependency of the pore solution temperature can be controlled or "sculpted" and measured directly, in real-time, via the change in the nanopore ionic conductance. The temperature change is highly localized near the pore, which allows the nanopore to probe the thermodynamic properties of single molecules.

Figure 1:
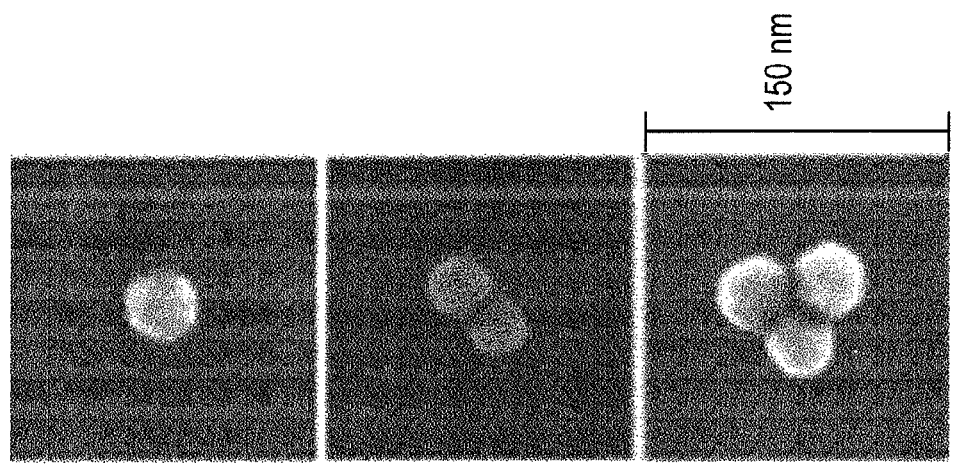
FIG. 1 is a schematic illustration of a system for controllably heating a nanopore or other small volume in accordance with the present subject matter.
Figure 1:
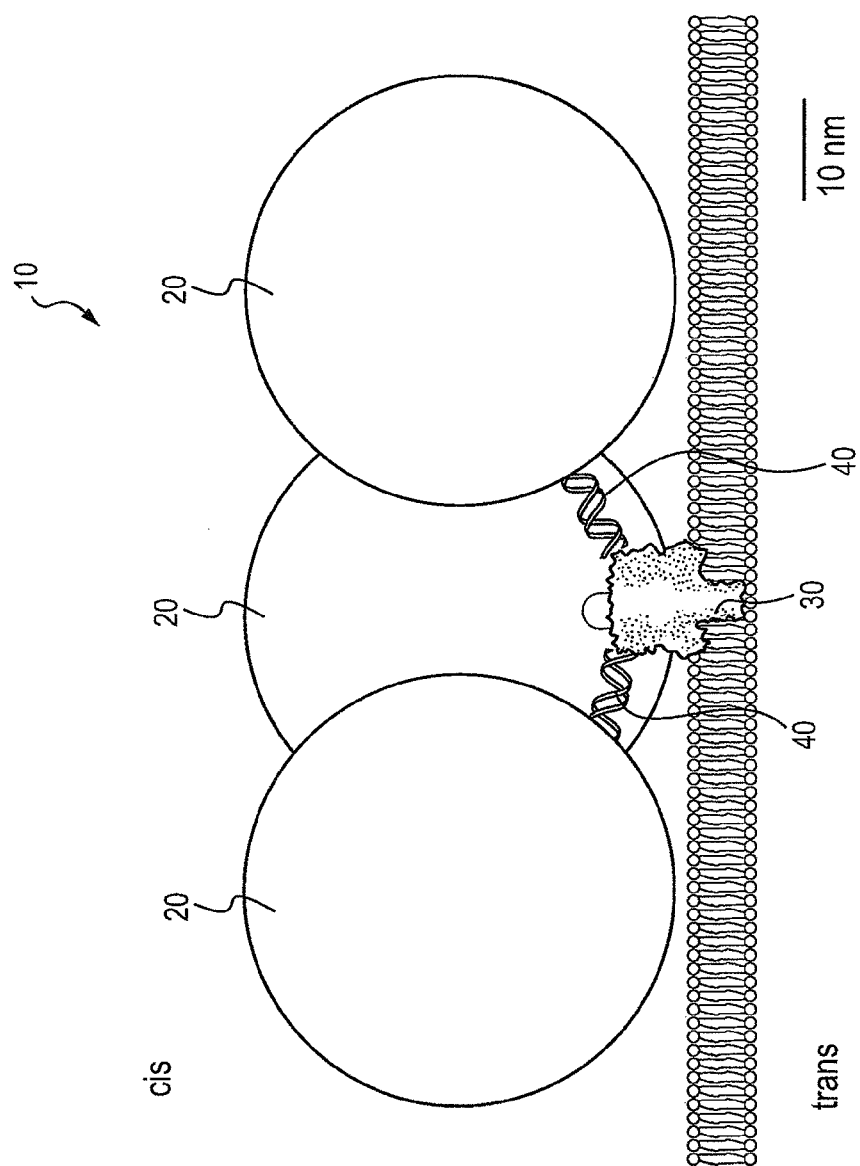

The feasibility of the present subject matter is demonstrated by linking one or more gold nanoparticles (40 nm diameter), via a DNA tether, to nanopores or protein ion channels formed by the protein toxin *Staphylococcus aureus* alpha hemolysin (αHL) in a planar lipid bilayer membrane or other biological layer as depicted in FIG. 1. Specifically, FIG. 1 is a schematic illustration of an approximate yoctoliter volume heating and measurement system 10 in accordance with the present subject matter. Forty nanometer diameter gold nanoparticles 20 are attached to a single nanopore or protein ion channel 30 formed by a genetically engineered version of the pore-forming toxin αHL, via 30 base pair duplex DNA. Tethers are depicted as 40. Continuous wave green laser light (532 nm) incident on the nanoparticles is strongly absorbed at or near the surface plasmon resonance, and raises their temperature. The temperature increase is determined from the change in the nanopore's ionic conductance. FIG. 1 also illustrates typical clusters of gold nanoparticles in the accompanying images. Statistical details are described herein in conjunction with FIGS. 7A-7D. Relatively short (30-nucleotide) DNA polynucleotides with a thiol group at the 5' end were bound to the nanoparticles. Complementary polynucleotides with a thiol group at the 3' end were attached to a genetically engineered αHL with a single asparagine (N) to cysteine point mutation at the amino-terminus (N293C), which is located on the cap domain of the ion channel. The duplex DNA separates each nanoparticle approximately 10 nm from the N terminus of the protein, and allows the attachment of up to three nanoparticles per channel, due to steric limitations. Although electrostatic repulsion can affect the configuration of the tethered Au nanoparticles in close proximity to each other, SEM imaging suggests this does not appear to be problematic (see FIGS. 1 and 7A-7D).

The rapid temperature increases made by illuminating or specifically, exciting surface plasmons of the gold nanoparticles with continuous wave 532 nm laser light, alters the electrolyte viscosity and thus bulk conductivity. This is deduced from the channel ionic conductance. That is, the temperature in and near the nanopore can be estimated from the channel ionic conductance. The relative change in the bulk conductivity is related to the temperature change by $\Delta\sigma/\sigma = A\Delta T$, where $A = 0.02°$ $C.^{-1}$ for initial temperatures of about $T_0 = 21°$ C., and is essentially independent of the electrolyte concentration. Because the αHL single channel conductance increases in proportion to the bulk conductivity, the αHL single channel conductance should increase in a like manner with temperature.

Figure 2A:
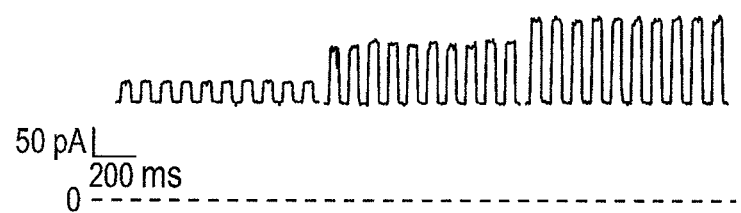
FIG. 2A shows conductance changes of a single nanopore caused by laser excitation of gold nanoparticles.
Figure 2B:
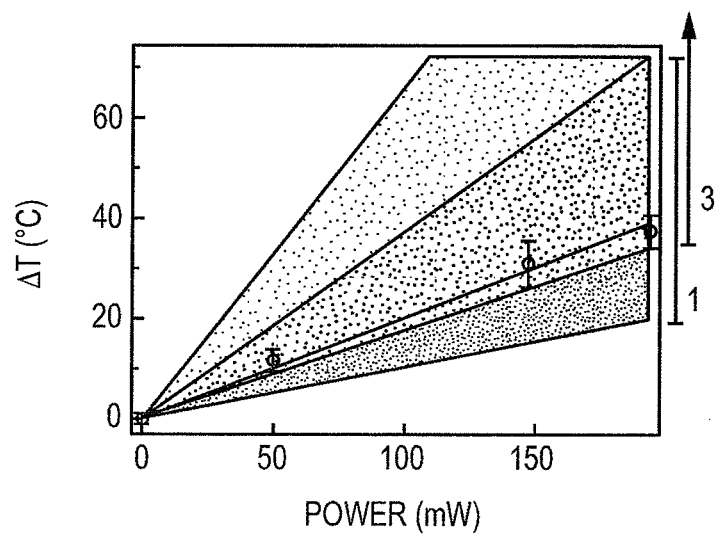
FIG. 2B is a graph illustrating temperature change as a function of applied laser power.
Figure 2C:
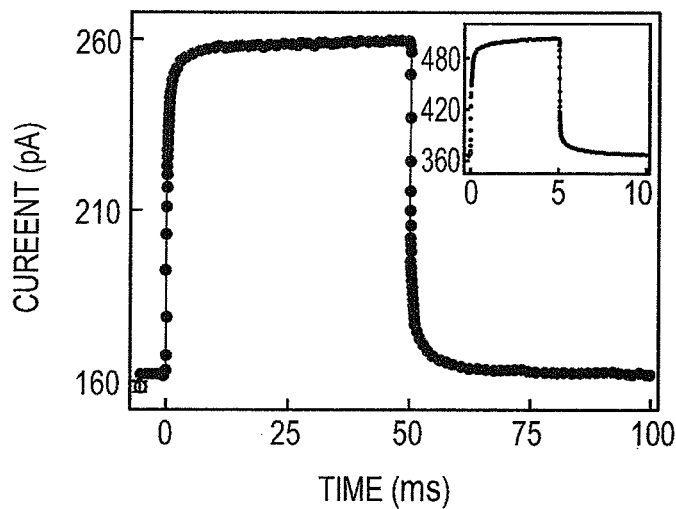
FIG. 2C is a graph of ionic current over time associated with a nanopore as described herein.

FIGS. 2A-2C illustrate control and measurement of the temperature in and around a nanopore. FIG. 2A shows conductance changes of a single nanopore caused by laser excitation of 40 nm diameter gold nanoparticles. The applied voltage was 40 mV and the on-off chopping frequency is 10 Hz. The detection bandwidth and sampling frequency are 10 kHz and 50 kHz, respectively. For the highest power setting a second nanopore or channel with an identical conductance appeared, and the current from that part of the data was divided by two. The slow variation in conductance in the heated states is likely caused by the movement of the system in the laser beam profile. FIG. 2B illustrates estimated temperature change with the applied laser power. The lower shaded region shows the calculated heating with standard deviation (SD) error estimate for a single nanoparticle attachment and the upper shaded region shows the three particle heating calculation and error estimate. In FIG. 2C, 390 current steps were aligned and averaged. A sigmoidal function was fit to these data in series with an exponential function (solid line) to yield two time constants. The excitation power was 147.5 mW and the ionic current was sampled at 50 kHz after filtering the data with a 10 kHz 4-pole low pass Bessel filter (FIG. 2C inset). 3,000 current steps of two nanopores were aligned and averaged to improve the signal to noise ratio and a sigmoidal function in series with two exponential functions (solid line) was fitted to this data to obtain three time constants. The excitation power was 180 mW, and the ionic current was sampled at 250 kHz after filtering the data with a 100 kHz 4-pole low pass Bessel filter.

Specifically, FIG. 2A shows a typical single nanopore ionic current time series at three different laser power levels. In each segment, the conductance steps are caused by cycling the laser beam on and off at a frequency of 10 Hz with an acousto-optic modulator.

FIG. 2B illustrates the linear increase in the nanopore temperature with the laser power, determined from the pore conductance. The calculated temperature change is overlaid for one (lower shaded region) and three (upper shaded region) nanoparticles attached to a nanopore. These data are suggestive of a single particle attachment but uncertainty in the calculation does not rule out either two or three particles bound to the channel.

In the presence of the nanoparticles, the mean ionic current in FIG. 2C shows that there are at least two relaxations in this particular system. The time constant for the heating and cooling phases of the investigation were determined by aligning and averaging multiple T-jumps, and fitting to the data a function that includes up to 3 series time constants. With a 10 Hz switching frequency, a steady state can be clearly observed within approximately 15 ms suggesting that the investigation is well controlled. Fitting these data produces two observable time constants, one at the bandwidth of the amplifier (0.1 ms) and a slower time constant of (1.16±0.05) ms for heating and (1.10±0.02) ms for cooling. The rise time for the change in temperature of the solution adjacent to a nanopore designated as T, is approximately 50 ns. The higher frequency switching data (100 Hz FIG. 2C inset) required a third time constant to produce a reliable fit. With $\tau_1$ held at the filter bandwidth (10 μs), additional time constants of (46.2±0.1) μs and (348±1) μs for the heating and (16.4±0.1) μs and (307±1) μs for the cooling are arrived at. While the observed time constants are much longer than the actual time it takes to heat the volume (approximately 50 ns), these results demonstrate the ability to directly observe, in real time, rapid changes of the temperature in a single nanopore. These long (relative to the solution rise time) relaxations are likely due to several nearly degenerate open states of the αHL nanopore, that may differ slightly from pore to pore, and do not impede the use of this method with suitably designed or chosen nanopores.

Figure 3:
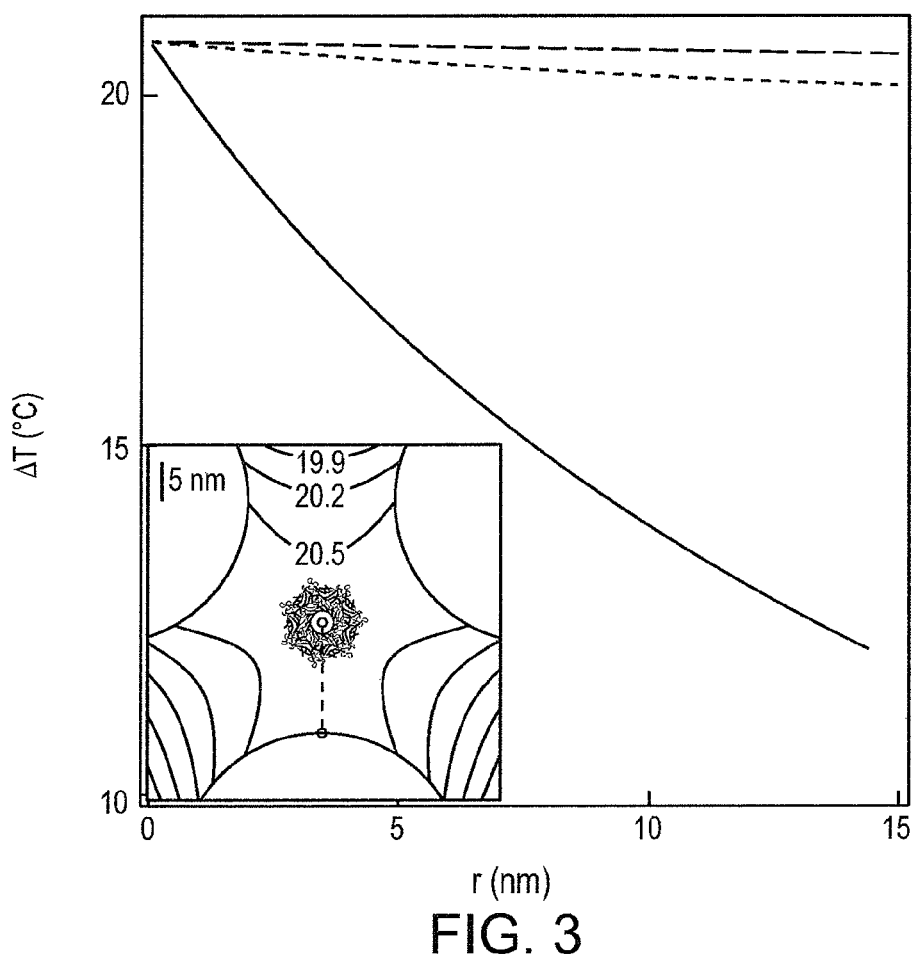
FIG. 3 is a graph illustrating theoretical temperature profiles adjacent to a nanopore with three tethered nanoparticles.

To confirm that the temperature changes result from heating nanoparticles directly attached to the nanopore, the temperature was calculated from the steady state heat equation with one, two, or three gold nanoparticles attached in the vicinity of the nanopore. The steady state heat equation is $\Delta^2 T + \kappa^{-1} q = 0$, and is used to calculate the increase in the solvent temperature above ambient, where κ is the thermal conductivity of the surrounding fluid and q is the power density absorbed by the gold particles. Here, convective and radiative heat transfer are ignored. Beginning with a single spherical nanoparticle, the temperature change above ambient is calculated to be $\Delta T = P_{abs}/[4\pi\kappa(r+a)]$ where $P_{abs}$ is the power absorbed by the particle, r is the radial distance measured from the surface of the nanoparticle, and a is the radius of the nanoparticle. In the Rayleigh limit, the temperature increase at the surface of the particle is $\Delta T_{particle}$ (0.4° C./mW)P, where P is the power incident on the nanoparticle. Using this result, the analysis is extended to the two and three particle cases by numerically solving the heat equation. For multiple particles, the temperature profile is calculated in the plane parallel to the membrane and defined by the centers of the particles (see FIG. 1), approximately 10 nm above the cis entrance of the nanopore. The profile of the calculated temperature increase above ambient for one, two, or three attached particles and P=49.7 mW is shown in FIG. 3. For the one particle case, the agreement between the estimated and calculated temperature is better than 5%. However, because of uncertainties in some of the measured parameters, the calculated temperature for two and three particles is also consistent with the measurements. Moreover for two or more particles, the temperature gradient from the particle surface is greatly reduced leading to an almost uniform temperature distribution adjacent to the nanopore. The net increase in nanopore conductance in proportion to the incident laser power is not due to smoothly varying changes to the pore's structure. The latter is comprised of seven anti-parallel β-sheets that are relatively stable over a wide range of temperatures (−10° C.<T<90° C.).

Specifically, FIG. 3 illustrates a theoretical temperature profile adjacent to a single αHL nanopore with three tethered 40 nm diameter gold nanoparticles, irradiated with 49.7 mW of 532 nm wavelength continuous wave laser light. The illustration shows the top view of the nanopore superimposed upon the temperature profile above ambient, calculated for the plane that connects the geometrical center of each sphere. This plane is approximately 10 nm above the cis entrance of the pore, see inset in FIG. 3. Temperature change above ambient as a function of distance from the surface of a nanoparticle assuming one (lower solid line), two (middle short dash line) and three (upper long dash line) nanoparticles attached to a pore. Due to spherical symmetry, the temperature estimate for a single particle is a function of the radial distance from the surface of the particle to the entrance of the pore. The temperature change estimate for two and three particles is limited to the plane of the calculation described above, and provides the upper limit of the expected temperature in the pore. The estimated temperature changes at the cis mouth of the pore for a single Au particle is 13.8° C., 41.1° C. and 54.3° C. for 49.7 mW, 147.5 mW and 195 mW excitations, respectively and 20.6° C., 61.4° C. and 81.5° C. for the same excitation power range for three Au particles. The uncertainty of this calculation is approximately 58% based on the uncertainty of 25% for the focal spot size, 10% for the particle size and 7% for the beam power, precluding an estimate number of particles attached for the experiments herein (see insert in FIG. 3).

Controlling the temperature in the vicinity of the nanopore detector enables single molecule thermodynamic and kinetic measurements because the ability of any polymer to enter the pore, and transport within the pore, should depend on the solution viscosity, and the polymer's thermodynamic properties. For example, an αHL nanopore can separate, with single monomer resolution, poly(ethylene glycol), PEG. Specifically, individual PEGs that enter the pore reduce the ionic conductance in proportion to the size of the polymer, and the amount of charge adsorbed to the polymer. PEG is an ideal candidate molecule with which to test this heating technique. It is currently the only polymer which has a detailed temperature-dependent physical model of the polymer inside the pore. Specifically, the residence time of PEGs inside the pore is strongly dependent on the ionic strength of the electrolyte solution. Weak chelation of cations by PEG plays a crucial role in this phenomenon. As such, this low energy barrier interaction is sensitive to temperature changes. Thus, the residence time of the PEG in the nanopore provides a continuous probe of the solution temperature within the nanopore and thus provides a secondary verification of the nanopore interior temperature independent of the open state current discussed earlier.

To test this hypothesis, monodisperse PEG (n=29, where n is the degree of polymerization) was added to the trans side of the membrane, and the incident heating laser power was cycled on and off at 10 Hz.

FIGS. 4A-4C illustrate effects of a temperature jump on PEG-induced effects on the single nanopore conductance. FIG. 4A shows ionic current time series for a single nanopore at T=21° C. (lower line $T_{room}$) and T=54° C. (upper line $T_{high}$) illustrating the transient PEG-induced decreases in nanopore conductance. A typical current blockade for each temperature state is shown (left). The pore conductance and PEG capture rate (events/sec) are greater at elevated temperature. FIG. 4B is a histogram of relative current blockades that shift to a lesser occluded state at elevated temperature. FIG. 4C is a histogram of the PEG residence times in the nanopore shifting to shorter-lived states, as predicted. The transmembrane potential was 40 mV.

Specifically, FIG. 4A shows the low and high conductance states of the open channel for conductance states at $T_{room}$= (21±1)° C. (lower line $T_{room}$) and T=(54±2)° C. (upper line $T_{high}$), respectively (the temperature steps have been removed and the high and low temperature segment have been concatenated for visual clarity). The ionic current time series (FIG. 4A) shows that the rate at which the PEGs enter the pore was greater at the elevated temperature (64 event/s and 24 event/s at T=54° C. and $T_{room}$=21° C., respectively). A representative single event from each T state is shown to the left. In addition, both the degree to which the PEG molecules blocked the pore conductance (FIG. 4B), and their mean residence times in the pore (260±30) µs and (88±4) µs, respectively (FIG. 4C), were less at the elevated temperature. At the higher temperature, PEG29 appears to have an additional characteristic relaxation time (approximately 0.7 ms). Because the events related to the longer time constant are Gaussian distributed, the transport mechanism causing those blockades is most likely different than the mechanism associated with the blockades with single exponential lifetime distributions (i.e., simple first-order kinetics).

The PEG capture rate increased by 2.7-fold while the nanopore conductance only increased by 1.6 fold in the higher temperature state (FIG. 4A). This enhanced capture rate can not be described solely by the decrease in solution viscosity. Another process or processes such as structural changes in the polymer or thermophoretic attraction may contribute to the enhanced capture rate. Regardless of the source of the enhanced polymer capture rate, the large temperature gradients present in these investigations should provide new means for developing and characterizing the thermodynamic properties of these and other polymer systems under as yet unexplored conditions.

Cations bound to PEG molecules in the pore have a profound effect on both the degree by which PEG reduces the pore conductance and the mean residence times for the polymers in the pore. Specifically, such cations cause a greater current blockade depth than PEG volume exclusion alone and they markedly increase the polymer residence time in the pore. Thus, the results in FIGS. 4B and 4C suggest that the increase in temperature decreases the number of cations bound to the PEG in the nanopore. Based on previously performed investigations and a theoretical model for cation-PEG interactions, the residence time of PEG29 in 3M solution should be (203±7) µs and (85±4) µs at the low and high temperatures used here, which is consistent with the data in FIGS. 4A-4C. In contrast to the results shown here (FIGS. 4A-4C), the magnitude of the current blockade predicted by the model is relatively insensitive to the temperature. This change in conductance is likely due to a change in the PEG conformation in the pore.

Figure 5:
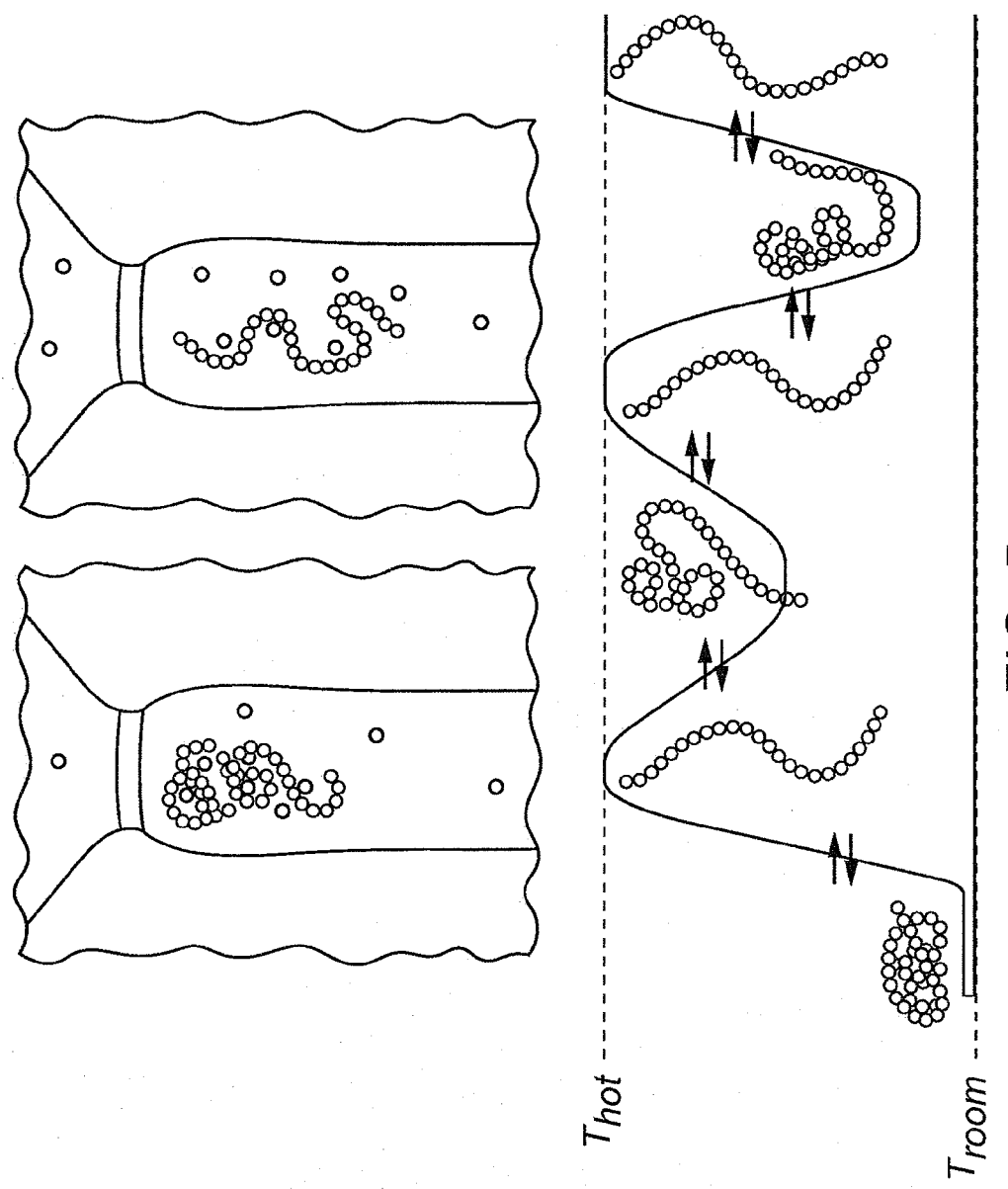
FIG. 5 illustrates representative conformations of molecules in nanopores at different temperatures.

FIG. 5 illustrates potential use of rapid temperature-jump kinetics for single molecule thermodynamic analysis. As illustrated in the top portion of FIG. 5, a polymer is drawn in the nanopore adopting two (of many) conformations that are affected by temperature. In this illustrative example, at room temperature, the polymer strongly interacts with cations, forming a tightly coiled structure. At elevated temperature the binding is relaxed and the polymer forms a less compact structure, as shown in the lower portion of FIG. 5. The ability to rapidly change the temperature profile (magnitude, duration, etc.) while a polymer is in the nanopore could help discriminate between subtly different molecules. Here, an investigation is envisioned where the equilibrium structure of a polymer is perturbed and measured with a well defined but variable thermal history.

Nanopore-based sensors are capable of detecting, identifying, and characterizing a wide range of molecular species, including ions, single-stranded RNA and DNA, double-stranded DNA, synthetic polymers, proteins, and proteins as they transition from the folded to the unfolded state both chemically and thermally. These results and the observation that single-stranded DNA and RNA can be driven electrophoretically through single nanopores or protein ion channels formed by αHL, stimulated research efforts into nanopores as single molecule sensors. Nanopores have been developed with a wide range of different chemistries from naturally occurring protein nanopores such as αHL, aerolysin, maltoporin, protective antigen, a membrane adapted phi29 motor protein or semiconductor based synthetic nanopores often formed in silicon nitride fabricated with either focused ion beams, TEM, or SEM. A useful property of nanopore detectors is that they are approximately yoctoliter volume devices that can measure single molecule-induced ionic current blockades with high signal-to-noise ratios. The ability to heat only this volume could bring single molecule T-jump methods to bear on nanopore-based analytical measurements and provide a marked advance in the technology. Using diffraction limited laser focal spots, which are considerably larger than nanopores ($10^{-16}$ L vs. $10^{-23}$ L, respectively), is problematic since they require high powers to initiate heating, comparable to the heating reported herein, and could lead to a number of problems including the rupture of the membrane supporting a protein nanopore.

One difficulty when heating samples with gold nanoparticles is accurately measuring the temperature surrounding the optically excited nanoparticles. Previous methods for deducing the temperature include measuring position fluctuations of an optically trapped gold nanoparticle, and observing phase transitions in a bilayer membrane or other matrix, or monitoring intensity fluctuations in laser-induced fluorescence. These optical methods require post-processing of data, which limits the ability to rapidly observe temperature changes and provide real-time estimates for, and control of the temperature. The methods of the present subject matter are different because the methods are electrical in nature and provide a direct measurement of the temperature adjacent to the nanoparticle. This allows for thermometry over timescales set by the integration time of the electrophysiology apparatus. More importantly, the methods of the present subject matter only measure the temperature of the solution within the approximately $10^{-23}$ L volume defined by the nanopore, which is the single molecule sensing region of interest.

By combining nanopore-based sensing with gold nanoparticle plasmon heating, the present subject matter provides a new approach for studying the thermodynamics and kinetics at the single molecule limit. The present subject matter includes methods and systems in which the properties of molecules are modified, via changes in temperature, within the vicinity of the nanopore for purposes of analysis and control. Such rapid changes would be impossible with standard heating technology. The methods of the present subject matter and described herein overcome these limitations by isolating the heating to a small volume (approximately yoctoliter) within a region of interest (nanopore sensor) for single molecule sensing.

Attachment of gold nanoparticles to single modified αHL nanopores and use of a system as both an effective single molecule heater and a nanometer-scale thermometer has been demonstrated. In addition, it has been shown that the gold-modified nanopore can perform single molecule sensing measurements with the temperature of the solution within the vicinity of the nanopore as a new variable under rapid control. Because the kinetics of reversibly heating such small volumes is extremely rapid (approximately 50 ns) compared to the residence times of polymers in single nanopores (approximately 1 ms), the methods of the present subject matter can clearly probe reversible equilibrium processes between different species and molecules that enter the pore (FIGS. 4A-4C). The present subject matter also has the potential to study the kinetics of structural changes that occur in synthetic and biological polymers by the use of complex temporal temperature profiles (FIG. 5) and to identify or discriminate between different molecules in solution, as has been demonstrated for the identification of gaseous species using micro-hotplates. For example, applying a complex temperature time series to the system should identify regimes of rapid or persistent rapid structural dynamics in different segments of the polymer. In this way, a convergence of single molecule kinetics and thermodynamics will reveal information about a polymer's identity, function, or both. Additional details associated with analyzing polymers at nanometer scale, are provided in Reiner et al., "Theory for Polymer Analysis Using Nanopore-Based Single-Molecule Mass Spectrometry," *PNAS*, Jul. 6, 2010, v. 107, no. 27, p. 12080.

Generally, the present subject matter provides systems for measuring temperature at a nanopore. The systems comprise a substrate that defines a first surface, and a biological layer disposed on the first surface of the substrate. The biological layer defines a second surface which typically also constitutes an outer exposed surface. The biological layer defines at least one nanopore. The systems also comprise a plurality of metallic nanoparticles tethered to the second surface of the biological layer. In certain embodiments, the metallic nanoparticles include gold nanoparticles. Typically, the nanoparticles have a size within a range of from about 10 nm to about 1,000 nm. At least a portion of the metallic nanoparticles are disposed proximate the nanopore. In certain embodiments, the metallic nanoparticles are tethered to the biological layer by at least one oligomer. The oligomer can be an oligonucleotide having from 10 to 500 repeating units, for example. The systems also comprise a light source such as a laser capable of generating light of sufficient intensity and wavelength to excite the metallic nanoparticles. Typically, the systems include an ionic conducting solution that bathes the nanopore and plasmonic structure(s). Nonlimiting examples of such conducting solutions include an electrolyte solution and/or ionic liquid. The systems additionally comprise an ionic current measuring system or assembly configured to measure changes in ionic conductance proximate to the nanopore. Upon excitation of the metallic nanoparticles resulting from emission of light from the light source, changes in ionic conductance measured by the ionic current measuring assembly are used to determine temperature or temperature changes at the nanopore.

The metallic nanoparticles of the present subject matter can include one or more metals such as gold, silver, platinum, palladium, ruthenium, rhodium, osmium, iridium, or other metals such as copper. Alloys or combinations of these and other metals are also contemplated. The present subject matter also includes the use of various semi-conductive materials for the nanoparticles such as cadmium selenide, cadmium telluride, zinc selenide, zinc telluride, cadmium phosphide, cadmium arsenide, gallium selenide, aluminum arsenide, and the like. The present subject matter also includes the use of combinations of metals and combinations of metals with non-metals.

The present subject matter includes nanoparticles having a relatively wide range of sizes such as from about 10 nm to about 1,000 nm. In certain embodiments, the nanoparticles have a size within a range of from about 25 nm to about 500 nm. In certain versions of the subject matter, the nanoparticles have a size of about 40 nm. However, it will be appreciated that the present subject matter includes the use of nanoparticles having sizes greater than or less than these sizes. In addition, it is contemplated that combinations of different sizes of nanoparticles may be used.

The nanoparticles of the present subject matter can have any of a variety of shapes including spherical, oblate, elongated, rod-shaped, wire-shaped, cubic, tetrahedral, octahedral, or another regular or irregular shape. A combination of metal nanoparticles having different shapes can be used. It is also contemplated that a wide array of forms for the nanoparticles may be used such as core-shell forms. In addition, the subject matter includes the use of aggregates of nanoparticles in nearly any form or combination.

The metallic nanoparticles can be attached or tethered to a substrate and particularly a biological layer or lipid layer on a substrate using a wide array of attachment provisions. In certain embodiments, the nanoparticles are attached using oligomers and particularly oligonucleotides having from about 10 to about 500 or in certain versions about 100, repeating units. In certain versions of the present subject matter, an oligonucleotide having approximately 30 repeating units is useful. However, it will be appreciated that the present subject matter includes other types of attachment provisions and oligomers having a lesser number and/or a greater number of repeating units.

The light source can be nearly any type of light source that is capable of generating light of sufficient intensity and wavelength to excite the plasmonic structure which may be for example one or more metallic nanoparticles. Nonlimiting examples of light sources include lasers, incandescent light sources, light emitting lodes, arc lamps, and combinations thereof.

Generally, the present subject matter also provides various methods. In one aspect, the subject matter provides methods for measuring temperature at a nanopore in a substrate and particularly in a biological layer. The methods comprise providing metallic nanoparticles. As previously noted, the metallic nanoparticles typically include gold nanoparticles. The metallic nanoparticles generally have a size within a range of from about 10 nm to about 1,000 nm. The methods also comprise tethering the metallic nanoparticles to the biological layer proximate the nanopore. Tethering can be performed by attaching the metallic nanoparticles to the biological layer using at least one oligomer. The oligomer can be an oligonucleotide having from 10 to 500 repeating units. The methods also comprise emitting light of sufficient intensity and wavelength to excite the metallic nanoparticles and induce a change in temperature. Emitting light can be performed by use of a laser. The methods also comprise measuring changes in ionic conductance proximate the nanopore. The changes in ionic conductance are used to determine temperature or temperature changes at the nanopore. In certain embodiments of the methods during emitting of the light, the light is absorbed at or near the surface plasmon resonance of the nanoparticles and increases the temperature of the nanoparticles. Specifically, in certain embodiments the light is absorbed at or near the surface plasmon resonance of plasmonic structure and increases the temperature of the plasmonic structure and the heat is conducted to an ionic conducting solution.

In another aspect, the subject matter provides methods for analyzing polymers. The methods comprise providing metallic nanostructures, as described herein. The methods also comprise providing a biological layer defining a nanopore. The methods additionally comprise tethering the metallic nanostructures to the biological layer proximate the nanopore. The methods also comprise disposing a polymer to be analyzed in the nanopore. And, the methods additionally comprise emitting light of sufficient intensity and wavelength such as for example by use of a laser, to excite the metallic nanostructures and induce a change in temperature within the nanopore. The change in temperature within the nanopore is used in analyzing the polymer disposed in the nanopore. In certain embodiments, the analyzing includes assessing at least one of (i) physical changes to polymers, (ii) chemical changes to polymers, (iii) thermodynamic properties of polymers, and (iv) kinetic properties of polymers. In certain embodiments, during the emitting of the light, the light is absorbed at or near the surface plasmon resonance and increases the temperature of the nanostructures.

EXAMPLES

Materials and Methods

Modification of Au Nanoparticles and N293C 40 nm diameter Au nanoparticles were attached to a genetically engineered version of the pore forming protein α-hemolysin, N293C with high melting temperature DNA oligonucleotides (30-mers) with a $T_m$ of approximately 120° C. 10 μL of 3.4 mM disulfide-protected DNA1 (5'-(5'-thiol)-GCGGCGCTCGCGGGCGCTGCGGCGGCGGCG-3') and its complimentary strand DNA2 (5'-(5'-thiol)-CGCCGC-CGCCGCAGCGCCCGCGAGCGCCGC-3') (Midland Certified Reagent Company, Midland, Tex.) in TE buffer (10 mM tris, 1 mM EDTA at pH 8.25), was mixed with 10 μL of 0.1 M dithiothreitol (DTT) and allowed to react at room temperature for 30 min. The deprotected DNA was then dialyzed with a 2 KDa molecular weight cut-off dialysis membrane (Slide-A-Lyzer Mini, 100 μL internal volume from Pierce/Thermo Scientific) into Milli-Q water (Millipore). To attach DNA1 to the pore forming protein N293C, 5 μL of 0.25 mg/mL (approximately 78 μM) N293C was added to 2 μL of deprotected DNA1 diluted to approximately 300 μM with 3.4 mg/mL bovine serum albumen (Sigma-Aldrich). To attach DNA2 to 40 nm Au nanoparticles, 10 μL of DNA2 was added to 20 μL of unprotected Au nanoparticles (Naked Gold, Bioassay Works, Ijamsville, Md.) (40±7) nm diameter with an optical density, OD=15, see FIG. 6A. The DNA conjugated protein and Au were stored in a refrigerator and used within one week.

Additional details for forming planar lipid bilayer membranes on substrates of PTFE are provided in Mueller et al., *J. Physical Chem,* 1963, 67, 534-535.

SEM Investigations

To image nanoparticle clusters attached to N293C, a lipid bilayer membrane was tethered to a gold electrode as described herein. About 1 nM DNA-modified αHL N293C was added to the solution, and allowed to form nanopores in the membrane for approximately 24 hours. The DNA-modified Au nanoparticles were subsequently injected into the solution and allowed to react for less than 1 min prior to vigorous rinsing with Milli-Q water. The surfaces were then removed from solution and dried with streaming $N_2$, and loaded into the SEM chamber for imaging.

Member Formation, Single Nanopore Capture, and Measuring Ionic Current

Planar lipid bilayer membranes were formed on an approximately 100 μm diameter hole formed in 25 μm thick PTFE. A prepaint mixture of 2 mg/mL DPhyPC in pentane was injected onto both sides of the hole and allowed to dry for approximately 10 minutes. The partition was then adhered onto a glass bottom Teflon holder. This allowed optical access and microscopic visualization of the membrane, e.g., a short working distance of approximately 100 µm between the top of the coverslip and the 100 µm hole. Electrolyte solution (3M KCl, 10 mM TRIS, pH 7.2) was added to the upper well and a femtotip (Eppendorf North America, Long Island, N.Y.) was positioned with a micromanipulator in close proximity to the hole. A few pL of lipid solution (5 mg/mL DPhyPC; hexadecane) was ejected from the tip onto the Teflon surface. A membrane was formed by dragging this solution across the hole with a small fire-polished glass rod. Specifically, a glass rod with a ball at the end was used to paint the lipid mixture over the hole. After several seconds the lipid thinned and formed a bilayer, which was verified both optically and through a capacitance measurement. A second femtotip containing the DNA-N293C solution was positioned in close proximity to the membrane. After positioning, a small backing pressure was applied to the femtotip (approximately 50-100 hPa) and a small transmembrane voltage was applied (typically 20 mV) to monitor the formation of nanopores into the membrane. After the insertion of about 100 to 1,000 nanopores, the backing pressure was reduced to zero and the tip was removed from the solution. DNA-modified Au nanoparticles were injected at the membrane surface in a similar fashion.

Finally, approximately 1 µm diameter glass pipette silanized with Sigmacote (Sigma Aldrich) containing a Ag/AgCl wire and matching electrolyte solution was brought into contact with the membrane until a single protein nanopore or ion channel was located within the inner tip. This localizes the nanopore to a well defined location and allows near-diffraction-limited laser excitation of the gold-modified nanopore. A 532 nm CW laser (Crystalaser, Reno, Nev.) operating at 300 mW was focused into the aperture of an acousto optic modulator (Crystal Technology, Palo Alto, Calif.). The modulator has a 20 ns risetime and the intensity of the first Bragg diffracted beam was modulated with a 15 MHz function generator (Agilent Technologies, Santa Clara, Calif.). An adjustable iris selected the first Bragg diffracted beam and this beam was launched into the back aperture of an inverted microscope (Axiovert 200, Zeiss). The beam was focused onto the end of the pipette with a 40× objective (EC Plan-Neofluar NA 0.9 Zeiss, Thornwood, N.Y.) to excite the plasmon mode of the nanoparticle and heat the surrounding solution. Measurement of the pore ionic conductance was performed with an Axopatch 200B and Digidata 1440A (Molecular Devices, Sunnyvale, Calif.). Unless reported otherwise, the ionic current data was sampled at 50 kHz with a 10 kHz low pass filter.

Additional details associated with measuring ionic conductance along a nanopore are provided in Robertson et al., "Single-Molecule Mass Spectrometry in Solution Using a Solitary Nanopore," *PNAS*, May 15, 2007, v. 104, no. 20, p. 8207.

Temperature Calculation

The temperature of each particle was calculated from the absorbed power $P_{abs}=I_b\eta_{abs}$, where $I_b=(P/\pi w_0^2)(1+(z\lambda/\pi w_0^2)^2)^{-1}$ is the intensity of the laser beam where P is the laser power incident on the particle, $w_0=(3\pm 0.75)$ µm is the beam waist, $\lambda=532$ nm is the laser wavelength and z is the axial distance of the particle from the focal plane. The Rayleigh absorption cross section is given by $\eta_{abs}=(6 n_w \pi V/\lambda) \text{Im}(\in_g-\in_w/\in_g+2\in_w)$ for a sphere of volume $V=4\pi\delta(a^2-2a\delta+2(1-\exp(-(a/\delta))\delta^2)$, skin depth $\delta=11$ nm at 532 nm wavelength and radius a=20 nm. The complex dielectric constant of the gold nanoparticles for 532 nm light is $\in_g=(-4.7+2.3\,i)$ and the water surrounding the particle is characterized by an electric permittivity $\in_w=1.77$ and index of refraction $n_w=1.33$. These parameters and equations give rise to the temperature of the particle described herein.

Control Investigations

Figure 6A:
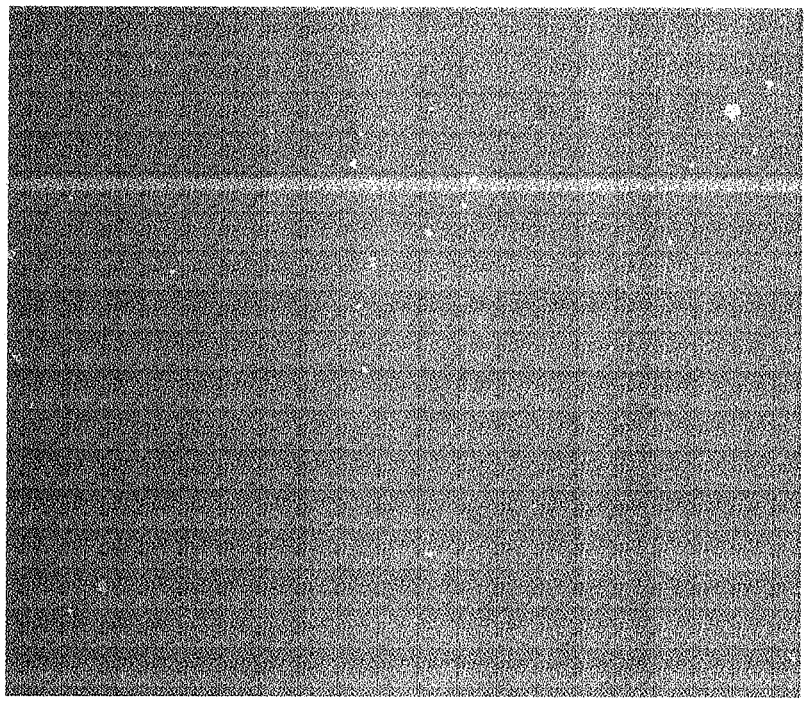
FIG. 6A is a representative image of gold nanoparticle aggregates after immobilization to a nanopore when both DNA-modified protein and DNA-modified Au are present.
Figure 6B:
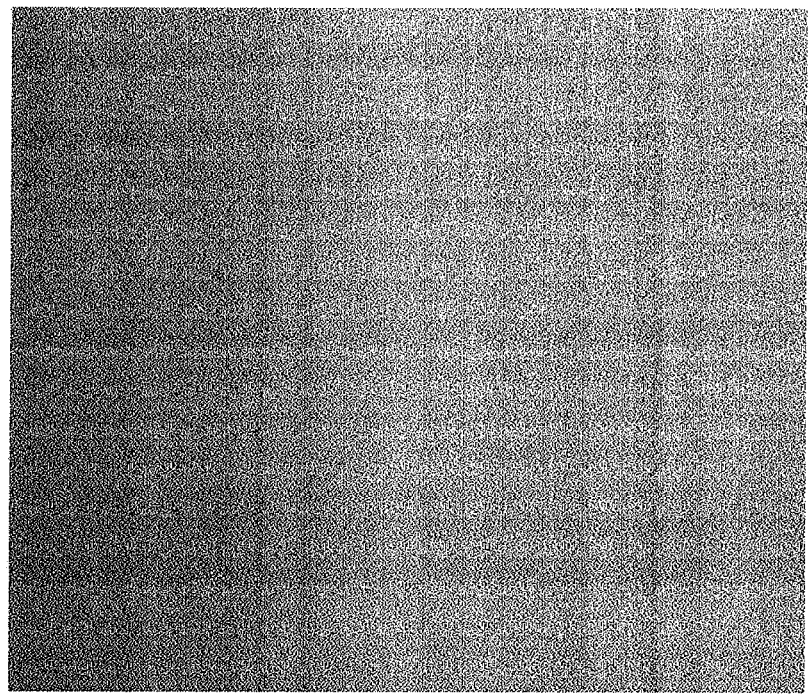
FIG. 6B is a representative image demonstrating gold nanoparticle immobilization when no protein is immobilized in the membrane.

To estimate the stoichiometry of the gold nanoparticles bound to single pores, and demonstrate the selective binding of gold nanoparticles to the mutated protein nanopores, a scanning electron microscopy (SEM) investigation was performed. Because the SEM operates in a high vacuum environment, a robust tethered bilayer membrane (tBLM) was prepared as the support for the protein-nanoparticle assembly. The essence of the tBLM is a self-assembled monolayer of synthetic lipid with a thiolated poly(ethylene glycol) spacer HC18 (Z 20-(Z-octadec-9-enyloxy)-3,6,9,12, 15,18,22-heptaoxatetracont-31-ene-1-thiol) diluted with β-mercaptoethanol, formed from a solution of 0.06 mM HC18/0.14 mM β-mercaptoethanol in ethanol. A bilayer was formed on this surface through the process of rapid solvent exchange. 20 µL of 10 mg/mL diphytanoylphosphocholine (DPhyPC) in ethanol was added to a dry monolayer surface and after 2 min, the solvent was exchanged with Milli-Q water (10 mL in approximately 1 min). This process results in a lipid bilayer supported on an approximately 3 nm thick polymer cushion which is amenable for αHL pore formation. 200 µL of about 1 nM DNA modified N293C αHL in a pH 5.5 buffer of 0.1 M KCl; and 10 mM Na(CH₃COO) was allowed to form nanopores for approximately 24 hr. DNA modified Au nanoparticles were injected into the solution well and immediately purged from solution by washing the surface with 10 mL of Milli-Q water. The modified surfaces were then dried with compressed air and transferred into the SEM for imaging. FIGS. 6A-6B display a collection of images from single particles through large aggregates suggesting that assembly of nanoparticles is not limited by electrostatic repulsion under the conditions described herein. A total of 32, approximately 100 µm² images (FIG. 6A) were collected resulting in 419 single particles, 219 double particles, 110 triple particles (57 clustered around a central point) and 299 larger aggregates (having more than 3 particles). A control sample in which DNA-modified Au was exposed to a membrane with no protein nanopores and vigorously washed from the cell showed no sign of Au nanoparticles, which suggests that a large fraction of the Au in the images was bound specifically to protein that was in the tBLM (FIG. 6B). Several controls verified that the changes in the channel conductance resulted from the heating of gold nanoparticles attached to the ion channel. These investigations illustrate the advantage of directly attaching the heating source to the ion channel and show that in the absence of direct attachment, temperature jumps reported by the nanopore are still possible (albeit with less reproducibility).

Figure 7A:
FIG. 7A illustrates ionic current over time for a negative control in which gold nanoparticles are not present, and no temperature change was observed.
Figure 7B:
FIG. 7B illustrates ionic current and thus temperature changes occurring for a system with two nanopores with attached gold nanoparticles.
Figure 7C:
FIG. 7C illustrates ionic current changes and associated temperature changes occurring for a system with a single nanopore adjacent to an attached large gold nanoparticle aggregate.
Figure 7D:
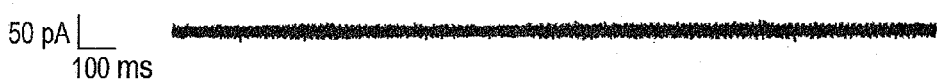
FIG. 7D illustrates ionic current for a system of a single nanopore with attached gold nanoparticles.

FIGS. 7A-7D show results from control experiments. FIG. 7A illustrates (approximately 205 mW 40× objective) a single N293C ion channel with no gold present and which was not heated by the laser. FIG. 7A illustrates the results of a negative control in which there are no gold nanoparticles present in the system. Specifically, the laser beam itself is not sufficient to cause the temperature increase. FIG. 7B shows two ion channels with 40 nm gold nanoparticles attached through a 10 nm DNA linker (data reproduced from FIG. 2A) at 197.4 mW, 40× objective, 10 Hz. FIG. 7C illustrates a single ion channel adjacent to a large gold nanoparticle aggregate anchored to the membrane with a thio-lipid at 14 mW, 10× objective, 50 Hz. FIG. 7D illustrates a single wt-αHL in a membrane with 40 nm Au nanoparticles specifically adsorbed to the membrane through a thio-lipid illuminated with 180 mW, 40× objective, 20 Hz.

Two positive controls were performed. Samples were prepared by first forming a monolayer of 20-tetra-decyloxy-3,6,9,12,15,18,22-heptaoxahexatricontane-1-thiol (WC14) on 40 nm Au nanoparticles. This monolayer essentially coats the nanoparticle with a lipid-monolayer which when injected from solution in the presence of a lipid bilayer allows the Au to specifically adsorb to the membrane. Using the high temperature data reproduced from FIG. 2A as a visual control in FIG. 7B, the heating observed by illuminating a large cluster of Au is shown in FIG. 7C (likely aggregated Au nanoparticles anchored to the membrane through WC14) and rivals the temperature changes reported herein, but with less stability in the high temperature state. It is likely that the αHL occasionally diffused near Au clusters in the membrane, and the distance between the heat source and the ion channel varied over the course of the investigation. When a lower density of Au is added to the membrane (FIG. 7D), there is little to no observable heating from isolated nanoparticles. This suggests that in the absence of any aggregation of Au nanoparticles, there is essentially no added heating due to Au that is not directly attached to the protein.

Figure 8:
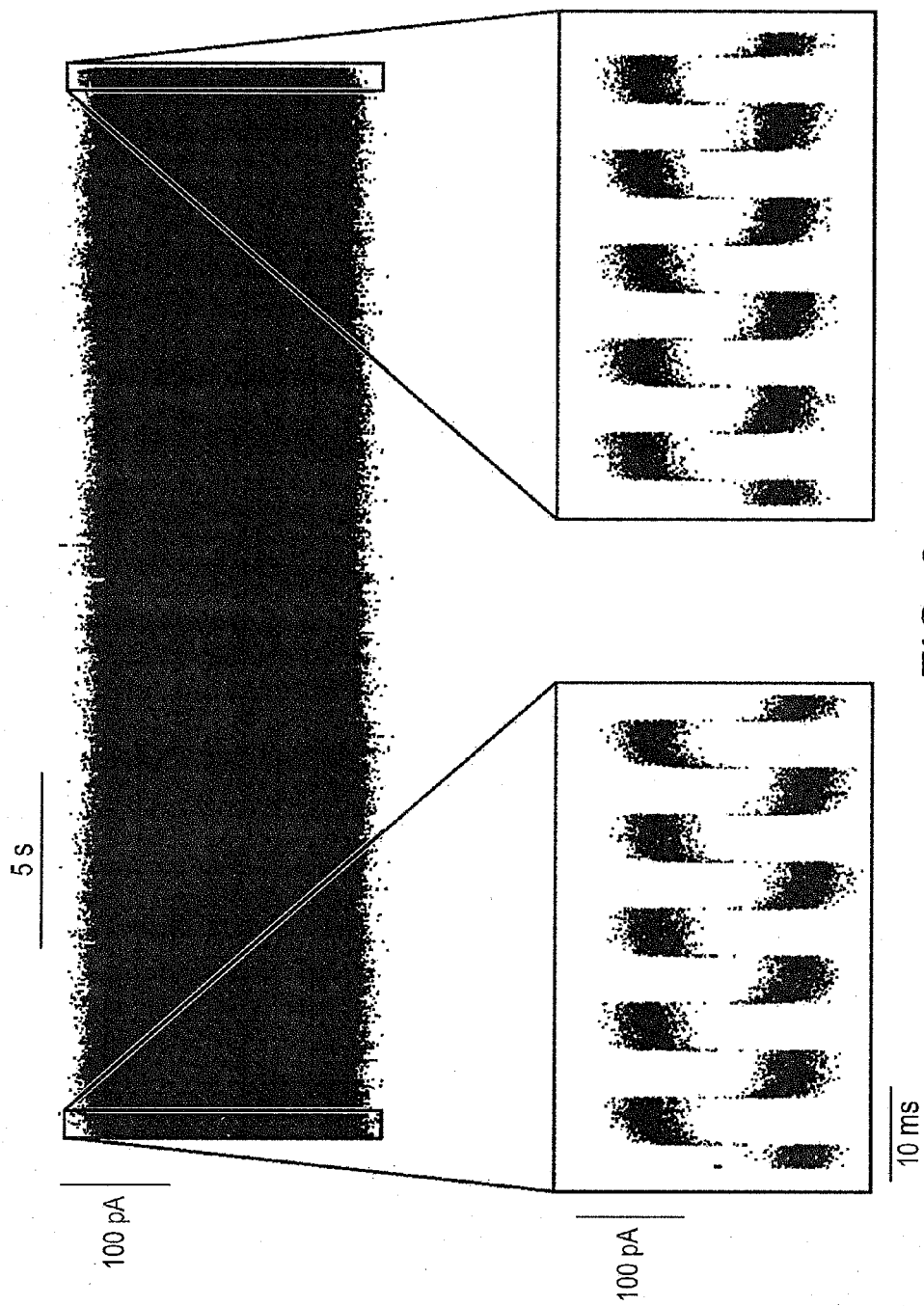
FIG. 8 illustrates relative stability of the nanopore ionic current over repeated temperature cycles.

FIG. 8 illustrates that the nanopore ionic current was stable over many repeated temperature cycles. The applied potential was 40 mV and the laser illumination was cycled on and off at 100 Hz.

Fitting Time Constants

The observed time constants for these investigations were estimated as a series of 2 time constants for the low frequency data and 3 time constants for the high frequency data. In each case, the fastest time constant was considered a sigmoidal function with τ equal to the bandwidth of the Bessel filter. The equation used was as follows:

$$\Delta I_{f(T)} = \alpha\left(\frac{1}{1+\exp\left(-\frac{t-\delta}{\tau_1}\right)} + \left(1-\exp\left(-\frac{t}{\tau_2}\right)\right) + \left(1-\exp\left(-\frac{t}{\tau_3}\right)\right)\right) + b$$

where $\Delta I_{f(T)}$ is the temperature dependent current, $\alpha$ is a scaling constant, t is the time from the temperature step, $\delta$ is a bandwidth-limited delay, $\tau_1$, $\tau_2$ and $\tau_3$ are time constants and b is a linear offset. To reduce the uncertainty and provide an estimate of the error temperature, steps were averaged prior to fitting to the equation. For the low frequency data 3 sets of 130 steps were fit and for the high frequency data 6 sets of 500 steps were fit. Error bars are the standard deviation of the estimated fit parameters. Estimated time constants using low and high frequency sampling are set forth below in Tables 1 and 2:

TABLE 1

Estimated Time Constant from a Single Channel with Low Frequency Sampling: 50 kHz Sampled Data/10 kHz Filtered

|  | $\alpha$<br>$\mu \pm 1\sigma$ (pA) | $\delta$<br>$\mu \pm 1\sigma$ (ms) | $\tau_1$<br>$\mu \pm 1\sigma$ (ms) | $\tau_2$<br>$\mu \pm 1\sigma$ (ms) |
|---|---|---|---|---|
| Up | 48.3 ± 0.3 | 0.51 ± 0.02 | 0.1 +/− 0.0 | 1.16 ± 0.05 |
| Down | −48.0 ± 0.1 | 0.41 ± 0.07 | 0.1 +/− 0.0 | 1.10 ± 0.02 |

TABLE 2

Estimated Time Constant from a Single Channel with High Frequency Sampling: 250 kHz Sampled Data/100 kHz Filtered

|  | $\alpha$<br>$\mu \pm 1\sigma$ (pA) | $\delta$<br>$\mu \pm 1\sigma$ (ms) | $\tau_1$<br>$\mu \pm 1\sigma$ (ms) | $\tau_2$<br>$\mu \pm 1\sigma$ (ms) | $\tau_3$<br>$\mu \pm 1\sigma$ (ms) |
|---|---|---|---|---|---|
| Up | 45 ± 1 | 0.055 ± 0.001 | 0.01 +/− 0.0 | 0.046 ± 0.001 | 0.348 ± 0.008 |
| Down | −44 ± 1 | 0.025 ± 0.001 | 0.01 +/− 0.0 | 0.016 ± 0.001 | 0.307 ± 0.005 |

Residence Time Estimation

To calculate the expected residence time of the PEG29 molecules in the nanopore, a model was used for PEG interactions with both the pore and cations. The following values were used for the parameters in the model: $k_B T_{room}$=25.4 meV, a*=1.23, b*=1.15, s$^+$=0.229, s$^{PEG}$=0.129, $\Delta G_o$=−52.0 meV, $\xi$=7.07 Vs/m, x=4.81 and $\Delta G_c$=1.03 meV modified from the original fit in 4M KCl in. Where $k_B T_{room}$ is the thermal energy at room temperature, a* and b* are effective diffusion coefficients given by a*=$(D_+^{\mathit{eff}}+D_-^{\mathit{eff}})/D_0$ and b*=$D_+^{\mathit{eff}}/D_0$ where $D_\pm^{\mathit{eff}}$ is the effective diffusion parameter in the PEG occupied region of the pore for cations (+) and anions (−) and $D_0$ is the diffusion coefficient for all ions in the unoccupied pore, s$^+$ is a correction factor for the electroosmotic force to the electrical force on a single cation, s$^{PEG}$ is a correction factor for the electroosmotic force to the electrical force on the entire PEG molecule, $\Delta G_o$ is the free energy of PEG-cation binding inside the pore, $\xi$ is the hydrodynamic drag term, x is the mean number of monomers bound to a single cation and $\Delta G_c$ is the free energy of confinement of polymer in the pore. While the model's fitting parameters might depend on the cation concentration, that possibility is ignored here and the KCl concentration was set to 3M and the temperature ($k_B T$) was adjusted accordingly. Nevertheless, this model reasonably explains the qualitative trend in the observed residence time as a function of solution temperature.

The present subject matter includes a wide array of variant aspects. For example, the nanopores can be biologically derived protein nanopores. The nanopores can be fabricated in a solid substrate. The nanopores can be fabricated using known semiconductor processing methods. Solid-state nanopores can be fabricated in many different materials including semiconductors, for example silicon nitride, diamond, etc; or insulators such as quartz or other glasses.

As previously noted, the plasmonic structures can be in an array of different forms and configurations. For example, the plasmonic structures can include one or more nanoparticles and particularly metallic nanoparticles and specifically gold nanoparticles. The metallic nanoparticles can be directly attached to the nanopore or can be attached proximate the nanopore. The plasmonic structure can include deposited structured films. Various techniques can be used to attach the metallic nanoparticles such as by using known "click chemistry" or any other chemical attachment method.

Many other benefits will no doubt become apparent from future application and development of this technology.

All patents, published applications, and articles noted herein are hereby incorporated by reference in their entirety.

As described herein, the present subject matter solves many problems associated with previous strategies, systems and/or devices. However, it will be appreciated that various changes in the details, materials and arrangements of components, which have been herein described and illustrated in order to explain the nature of the present subject matter, may be made by those skilled in the art without departing from the principle and scope of the claimed subject matter, as expressed in the appended claims.

What is claimed is:

1. A system for measuring temperature at a nanopore, the system comprising:
   a substrate defining a surface and at least one nanopore;
   a plasmonic structure disposed proximate the nanopore;
   an ionic conducting solution which bathes the nanopore and the plasmonic structure;
   a light source capable of emitting light of sufficient intensity and wavelength to excite the plasmonic structure;
   an ionic current measuring assembly configured to measure changes in ionic conductance proximate to the nanopore;
   whereby upon excitation of the plasmonic structure resulting from emission of light from the light source, changes in ionic conductance measured by the ionic current measuring assembly are used to determine temperature or temperature changes at the nanopore.

2. The system of claim 1 where the substrate includes a biological layer disposed on the surface of the substrate, the biological layer defining a second surface and at least one nanopore, and the plasmonic structure including one or more metallic nanoparticles tethered to the second surface of the biological layer.

3. The system of claim 2 wherein the nanoparticles have a size within a range of from about 10 nm to about 1,000 nm.

4. The system of claim 2 wherein the metallic nanoparticles are tethered to the biological layer by at least one oligomer.

5. The system of claim 4 wherein the oligomer is an oligonucleotide having from 10 to 500 repeating units.

6. The system of claim 1 wherein the light source is selected from the group consisting of a laser, an incandescent light source, a light emitting diode, and an arc lamp.

7. The system of claim 1 wherein the ionic conducting solution is an electrolyte solution.

8. The system of claim 1 wherein the ionic conducting solution is an ionic liquid.

9. A method for measuring temperature at a nanopore, the method comprising:
   providing a plasmonic structure;
   affixing the plasmonic structure proximate the nanopore;
   emitting light of sufficient intensity and wavelength to excite the plasmonic structure and induce a change in temperature;
   measuring changes in ionic conductance proximate the nanopore;
   whereby the changes in ionic conductance are used to determine temperature or temperature changes at the nanopore.

10. The method of claim 9 wherein during emitting of the light, the light is absorbed at or near the surface plasmon resonance of the plasmonic structure and increases the temperature of the plasmonic structure and the heat is conducted to the ionic conducting solution.

11. The method of claim 9 wherein the plasmonic structures include metallic nanoparticles.

12. The method of claim 11 wherein the metallic nanoparticles have a size within a range of from about 10 nm to about 1,000 nm.

13. The method of claim 9 wherein the emitting light is performed using a light source selected from the group consisting of a laser, an incandescent light source, a light emitting diode, and an arc lamp.

14. The method of claim 9 wherein the plasmonic structure includes metallic nanoparticles and the nanopore is defined in a biological layer, wherein affixing is performed by attaching the metallic nanoparticles to the biological layer using at least one oligomer.

15. The method of claim 14 wherein the oligomer is an oligonucleotide having from 10 to 500 repeating units.

* * * * *